(12) United States Patent
Wald

(10) Patent No.: US 12,060,577 B2
(45) Date of Patent: Aug. 13, 2024

(54) COMPOSITIONS FOR EXPANDING NATURAL KILLER CELLS

(71) Applicant: CASE WESTERN RESERVE UNIVERSITY, Cleveland, OH (US)

(72) Inventor: David N. Wald, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 919 days.

(21) Appl. No.: 16/614,132

(22) PCT Filed: May 21, 2018

(86) PCT No.: PCT/US2018/033668
§ 371 (c)(1),
(2) Date: Nov. 15, 2019

(87) PCT Pub. No.: WO2018/213828
PCT Pub. Date: Nov. 22, 2018

(65) Prior Publication Data
US 2020/0199532 A1 Jun. 25, 2020

Related U.S. Application Data

(60) Provisional application No. 62/508,666, filed on May 19, 2017, provisional application No. 62/538,961, filed on Jul. 31, 2017, provisional application No. 62/578,742, filed on Oct. 30, 2017.

(51) Int. Cl.
*A61K 35/17* (2015.01)
*C07K 14/54* (2006.01)
*C12N 5/0783* (2010.01)

(52) U.S. Cl.
CPC ............ *C12N 5/0646* (2013.01); *A61K 35/17* (2013.01); *C07K 14/54* (2013.01); *C12N 2501/2302* (2013.01); *C12N 2501/2312* (2013.01); *C12N 2501/2315* (2013.01); *C12N 2501/2318* (2013.01); *C12N 2501/2321* (2013.01); *C12N 2502/30* (2013.01); *C12N 2510/00* (2013.01)

(58) Field of Classification Search
CPC .......... C12N 5/0646; C12N 2501/2321; C07K 14/54; A61K 38/20
See application file for complete search history.

(56) References Cited

U.S. PATENT DOCUMENTS

| | | |
|---|---|---|
| 2006/0023641 A1 | 2/2006 | Nakashima et al. |
| 2006/0067920 A1 | 3/2006 | Jensen |
| 2006/0269516 A1 | 11/2006 | Presta et al. |
| 2015/0071987 A1 | 3/2015 | Selvaraj |
| 2017/0073638 A1 | 3/2017 | Campana et al. |

FOREIGN PATENT DOCUMENTS

| | | | |
|---|---|---|---|
| CN | 108300697 A | * | 7/2018 |
| WO | 2015017214 A1 | | 2/2015 |
| WO | 2015154012 A1 | | 10/2015 |
| WO | 2016061344 A1 | | 4/2016 |
| WO | 2016161410 A2 | | 10/2016 |
| WO | 2017040945 A1 | | 3/2017 |

OTHER PUBLICATIONS

Lim et al. Ex vivo expansion of highly cytotoxic human NK cells by cocultivation with irradiated tumor cells for adoptive immunotherapy. Cancer Res. Apr. 15, 2013;73(8):2598-607.*
Xu et al. DNMT3A mutation leads to leukemic extramedullary infiltration mediated by TWIST1. J. Hematol. Oncol. Oct. 10, 2016;9(1):106.*
Lowdell, M.W. Natural killer cells in haematopoietic stem cell transplantation. Transfusion Medicine 2003;13:399-404.
Berg M, et al. Clinical-grade ex vivo-expanded human natural killer cells up-regulate activating receptors and death receptor ligands and have enhanced cytolytic activity against tumor cells. Cytotherapy. 2009;11(3):341-55.
Tonn T, et al. Treatment of patients with advanced cancer with the natural killer cell line NK-92. Cytotherapy. 2013;15(12):1563-70.
Denman CJ, et al. Membrane-bound IL-21 promotes sustained ex vivo proliferation of human natural killer cells. PloS one. 2012;7(1):e30264.
Spanholtz, et al. High log-scale expansion of functional human natural killer cells from umbilical cord blood CD34-positive cells for adoptive cancer immunotherapy. PloS one. 2010;5(2):e9221.
Chen, R.H. et al. Inactivation of the type II receptor reveals two receptor pathways for the diverse TGF-beta activities. Science 1993;260(5112):1335-1338.
Kloss, C. et al. TGFBeta Signaling Blockade within PSMA Targeted CAR Human T Cells for the Eradication of Metastatic Prostate Cancer. Molecular Therapy 2016;24(S1): S252-S253.).
Quentmeier et al. "Cell line OCI/AML3 bears exon-12 NPM gene mutation-A and cytoplasmic expression of nucleophosmin," Leukemia, Aug. 4, 2005 (Aug. 4, 2005), vol. 19, pp. 1760-1767. entire document.
Fujisaki et al. "Expansion of Highly Cytotoxic Human Natural Killer Cells for Cancer Cell Therapy," Cancer Research, Apr. 21, 2009 (Apr. 21, 2009), vol. 69, No. 9, pp. 4010-4017. entire document.

(Continued)

*Primary Examiner* — Dong Jiang
(74) *Attorney, Agent, or Firm* — Pearne & Gordon LLP

(57) ABSTRACT

The present disclosure relates to methods for expanding and increasing the cytotoxic activity of natural killer cells comprising co-culturing, as feeder cells, a population of myeloid leukemia cells engineered to express one or more of membrane-bound IL-21 (mb IL-21) or membrane-bound IL-15 (mbIL-15) in the presence of cytokine support. The present disclosure also relates to a population of acute myeloid leukemia cells engineered to express one or more of membrane-bound IL-21 (mbIL-21) or membrane-bound IL-15 (mbIL-15). The present disclosure also relates to methods of treating cancer employing the step of expanding natural killer cells using feeder cells engineered to express one or more of membrane-bound IL-21 (mbIL-21) or membrane-bound IL-15 (mbIL-15).

6 Claims, 13 Drawing Sheets
Specification includes a Sequence Listing.

(56) References Cited

OTHER PUBLICATIONS

Alici et al. "Autologous antitumor activity by NK cells expanded from myeloma patients using GMP-compliant components," Blood, Mar. 15, 2008 (Mar. 15, 2008), vol. 111, No. 6, pp. 3155-3162. entire document.

Sarvaria et al. "Umbilical Cord Blood Natural Killer Cells, Their Characteristics, and Potential Clinical Applications," Frontiers in Immunology, Mar. 23, 2017 (Mar. 23, 2017), vol. 8, Article 329, pp. 1-6. entire document.

Otegbeye, et al.; Inhibiting TGF-beta signaling preserves the function of highly activated, in vitro expanded natural killer cells in AML and colon cancer models; Research Article, https://doi.org/10.1371/journal.pone.191358; Jan. 17, 2018.

Parameswara, et al.; Repression of GSK3 restores NK cell cytotoxicity in AML patients; Nature Communications; DOI: 10.1038/ncomms11154; Apr. 4, 2016.

Wagner, et al.; A Two-Phase Expansion Protocol Combining Interleukin (IL)-15 and IL-21 Improves Natural Killer Cell Proliferation and Cytotoxicity against Rhabdomyosarcoma; Frontiers in Immunology; vol. 8; Article 676; Jun. 2017.

Zhu, et al.; Novel Human Interleukin-15 Agonists; The Journal of Immunology; Sep. 15, 2009, 183 (6) 3598-3607; www.jimmunol.org./cgi/doi/10.4049/jimmunol.0901244; 2009.

The International Search Report and Written Opinion issued in correspondence International PCT Application No. PCT/US208/033668; Mailing Date: Aug. 10, 2018.

The Search Report issued in corresponding European Patent Application No. 18801559.8; Mailing Date: Oct. 20, 2020.

\* cited by examiner

US 12,060,577 B2

SEQUENCE LISTING

```
<160> NUMBER OF SEQ ID NOS: 7

<210> SEQ ID NO 1
<211> LENGTH: 395
<212> TYPE: PRT
<213> ORGANISM: Artificial Sequence
<220> FEATURE:
<223> OTHER INFORMATION: Synthetic construct mbIL-21

<400> SEQUENCE: 1

Met Leu Leu Leu Val Thr Ser Leu Leu Leu Cys Glu Leu Pro His Pro
1               5                   10                  15

Ala Phe Leu Leu Ile Pro Gln Asp Arg His Met Ile Arg Met Arg Gln
            20                  25                  30

Leu Ile Asp Ile Val Asp Gln Leu Lys Asn Tyr Val Asn Asp Leu Val
        35                  40                  45

Pro Glu Phe Leu Pro Ala Pro Glu Asp Val Glu Thr Asn Cys Glu Trp
    50                  55                  60

Ser Ala Phe Ser Cys Phe Gln Lys Ala Gln Leu Lys Ser Ala Asn Thr
65                  70                  75                  80

Gly Asn Asn Glu Arg Ile Ile Asn Val Ser Ile Lys Lys Leu Lys Arg
                85                  90                  95

Lys Pro Pro Ser Thr Asn Ala Gly Arg Arg Gln Lys His Arg Leu Thr
            100                 105                 110

Cys Pro Ser Cys Asp Ser Tyr Glu Lys Lys Pro Pro Lys Glu Phe Leu
        115                 120                 125
```

Glu Arg Phe Lys Ser Leu Leu Gln Lys Val Ser Thr Leu Ser Phe Ile
130                 135                 140

Glu Ser Lys Tyr Gly Pro Pro Cys Pro Pro Cys Pro Ala Pro Glu Phe
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser Gln Glu Asp Pro Glu Val Gln Phe Asn Trp Tyr Val Asp Gly Val
            195                 200                 205

Glu Val His Asn Ala Lys Thr Lys Pro Arg Glu Glu Gln Phe Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Gly Leu Pro Ser
                245                 250                 255

Ser Ile Glu Lys Thr Ile Ser Lys Ala Lys Gly Gln Pro Arg Glu Pro
            260                 265                 270

Gln Val Tyr Thr Leu Pro Pro Ser Gln Glu Glu Met Thr Lys Asn Gln
            275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Arg Leu
                325                 330                 335

Thr Val Asp Lys Ser Arg Trp Gln Glu Gly Asn Val Phe Ser Cys Ser
            340                 345                 350

Val Met His Glu Ala Leu His Asn His Tyr Thr Gln Lys Ser Leu Ser
            355                 360                 365

Leu Ser Leu Gly Lys Met Ala Leu Ile Val Leu Gly Gly Val Ala Gly
            370                 375                 380

Leu Leu Leu Phe Ile Gly Leu Gly Ile Phe Phe
385                 390                 395

<210> SEQ ID NO 2
<211> LENGTH: 1185
<212> TYPE: DNA
<213> ORGANISM: Artificial Sequence
<220> FEATURE:
<223> OTHER INFORMATION: Synthetic construct mbIL-21

<400> SEQUENCE: 2
atgctcttgc tcgtcacctc cttgctgctg tgtgaactgc cgcaccctgc gttccttctt      60
attccacagg accgacacat gatccgaatg cgccaactca tagacatcgt agaccagctc     120
aagaattatg tcaacgacct ggtgcctgag ttcctcccgg ctccagagga cgtcgaaaca     180
aactgcgaat ggtctgcttt tagctgtttt caaaaggcgc agttgaaatc agcgaacacg     240
ggcaataatg agcgcattat taacgtctca atcaagaaac tgaaaagaaa gccaccgtca     300
acaaatgctg gcgacggca gaaacataga cttacctgcc caagctgtga ctcctacgag     360
aaaaagccgc gaaagagtt tcttgaaagg ttcaagagcc tcctccagaa ggtgtctacc     420
ctgagcttca tcgaatccaa gtacggtccc catgtccccc gtgcccgc ccctgagttt      480 ctgggggtc cttcagtttt tctgttcccg ccaaagccaa aggacactct gatgatatcc     540

-continued

```
agaacaccgg aggttacttg tgtcgtggtc gatgttagcc aagaggaccc cgaagttcag    600
ttcaactggt atgtcgacgg cgtggaagtc cataatgcaa aaacgaaacc acgggaagag    660
caattcaata gcacctacag agtagtatca gttctgaccg ttctgcatca agactggctc    720
aacggtaaag aatacaagtg caaagtgtct aataaaggct tgcctagttc catagaaaag    780
accatcagca aggcgaaagg gcaaccacga gagccacaag tctatacgct tcccccatca    840
caagaagaaa tgacgaagaa ccaagtgagc ttgacgtgct tggtgaaggg ttttacccg    900 tcagacatag ccgtcgagtg ggaatcaaat ggccagcccg agaacaatta caaaacaact    960
ccacccgttc tcgactccga cggttccttt tcctctact cacgattgac tgtagataag    1020
agcagatggc aagagggaaa tgtgttctct tgtagcgtga tgcacgaagc actccataac   1080
cactacactc agaaatcact ctctctcagt cttgggaaaa tggcactcat tgtgctcggt    1140
ggggtggcag gtcttcttct gtttattggc cttggaatat ttttc                   1185
```

<210> SEQ ID NO 3
<211> LENGTH: 387
<212> TYPE: PRT
<213> ORGANISM: Artificial Sequence
<220> FEATURE:
<223> OTHER INFORMATION: Synthetic construct mbIL-15

<400> SEQUENCE: 3

```
Met Leu Leu Leu Val Thr Ser Leu Leu Leu Cys Glu Leu Pro His Pro
1               5                   10                  15

Ala Phe Leu Leu Ile Pro Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Glu Ser Lys Tyr Gly Pro Pro Cys
    130                 135                 140

Pro Pro Cys Pro Ala Pro Glu Phe Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser Gln Glu Asp Pro Glu Val Gln
            180                 185                 190

Phe Asn Trp Tyr Val Asp Gly Val Glu Val His Asn Ala Lys Thr Lys
        195                 200                 205

Pro Arg Glu Glu Gln Phe Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Gly Leu Pro Ser Ser Ile Glu Lys Thr Ile Ser Lys
                245                 250                 255
```

Ala Lys Gly Gln Pro Arg Glu Pro Gln Val Tyr Thr Leu Pro Pro Ser
            260                 265                 270

Gln Glu Glu Met Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Arg Leu Thr Val Asp Lys Ser Arg Trp Gln
                325                 330                 335

Glu Gly Asn Val Phe Ser Cys Ser Val Met His Glu Ala Leu His Asn
            340                 345                 350

His Tyr Thr Gln Lys Ser Leu Ser Leu Ser Leu Gly Lys Met Ala Leu
        355                 360                 365

Ile Val Leu Gly Gly Val Ala Gly Leu Leu Leu Phe Ile Gly Leu Gly
    370                 375                 380

Ile Phe Phe
385

<210> SEQ ID NO 4
<211> LENGTH: 1164
<212> TYPE: DNA
<213> ORGANISM: Artificial Sequence
<220> FEATURE:
<223> OTHER INFORMATION: Synthetic construct mbIL-15

<400> SEQUENCE: 4

| | |
|---|---|
| atgctgcttc tcgtaacgtc cttgttgttg tgcgaattgc ctcatccagc attcttgctt | 60 |
| attcccaact gggtcaacgt aataagtgac ttgaaaaaaa tcgaggatct gatacagagt | 120 |
| atgcacatcg atgcaacact ctacactgag agtgatgttc acccgagttg taaagtgaca | 180 |
| gcgatgaaat gttttcttct tgaacttcag gttatatcac ttgaatcagg tgatgctagt | 240 |
| atccatgaca cggtggagaa tctcatcatt cttgctaata acagtctctc ctcaaatggt | 300 |
| aatgtaacag aatctggctg taaagaatgc gaggaattgg aggagaagaa cataaaggaa | 360 |
| tttctccaga gcttcgtcca tatagtacag atgttcatca acacatccga gtctaaatac | 420 |
| ggcccgccgt gtccaccgtg tccagcgcca gagtttctcg gtggcccttc tgtgttcctg | 480 |
| ttcccccca gcccaaaga taccettatg atatcaagaa caccagaagt cacttgtgtc | 540 |
| gttgtcgatg tgagccaaga agaccctgag gtacagttca actggtatgt agatggggtt | 600 |
| gaggttcata acgccaaaac taagcccaga gaagaacaat caatagtac ttatagagtt | 660 |
| gtctcagtac ttacggtctt gcatcaagat tggttgaatg gtaaggaata taagtgcaaa | 720 |
| gtgtccaata agggcctgcc aagcagtata gagaagacta tctccaaggc aaaagggcaa | 780 |
| ccccgcgaac cacaggtcta tactcttcca cccagccaag aggaaatgac taaaaatcaa | 840 |
| gtatctctta cgtgccttgt gaaaggtttt tacccgagtg atattgccgt agagtgggaa | 900 |
| tccaacggcc agccagagaa caactataag actacgccgc cggtttggga tagtgacggc | 960 |
| tccttctttc tgtactccag gctcacggtc gacaagagtc gatggcaaga ggggaacgta | 1020 |
| tttagttgct ctgtgatgca tgaagcgctg cacaatcatt atactcagaa gagtctgtcc | 1080 |
| ctgagtctcg gcaaaatggc cctgattgta ctgggagggg ttgctggact tctcctgttt | 1140 |
| atcggactcg gtatcttctt ctga | 1164 |

<210> SEQ ID NO 5
<211> LENGTH: 9680
<212> TYPE: DNA
<213> ORGANISM: Artificial Sequence
<220> FEATURE:
<223> OTHER INFORMATION: Synthetic construct

<400> SEQUENCE: 5

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcgggggaga | 600 |
| attagatcgc | gatgggaaaa | aattcggtta | aggccagggg | gaaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | gaataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |
| ggcaagaatc | ctggctgtgg | aaagatacct | aaaggatcaa | cagctcctgg | ggatttgggg | 1320 |
| ttgctctgga | aaactcattt | gcaccactgc | tgtgccttgg | aatgctagtt | ggagtaataa | 1380 |
| atctctggaa | cagatttgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcgcta | 1800 |
| gcttttaaaa | gaaaaggggg | gattggggggg | tacagtgcag | gggaaagaat | agtagacata | 1860 |
| atagcaacag | acatacaaac | taagaattac | aaaaacaaa | ttacaaaaat | tcaaaatttt | 1920 |
| actagtgatt | atcggatcaa | ctttgtatag | aaaagttggg | ctccggtgcc | cgtcagtggg | 1980 |
| cagagcgcac | atcgcccaca | gtccccgaga | agttgggggg | aggggtcggc | aattgaaccg | 2040 |
| gtgcctagag | aaggtggcgc | ggggtaaact | gggaaagtga | tgtcgtgtac | tggctccgcc | 2100 |

```
tttttcccga gggtggggga gaaccgtata taagtgcagt agtcgccgtg aacgttcttt    2160
ttcgcaacgg gtttgccgcc agaacacagg taagtgccgt gtgtggttcc cgcgggcctg    2220
gcctctttac gggttatggc ccttgcgtgc cttgaattac ttccacctgg ctgcagtacg    2280
tgattcttga tcccgagctt cgggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtggcacctt cgcgcctgtc tcgctgcttt cgataagtct ctagccattt    2460
aaaattttg atgacctgct gcgacgcttt ttttctggca agatagtctt gtaaatgcgg    2520
gccaagatct gcacactggt atttcggttt tggggccgc gggcggcgac ggggcccgtg    2580
cgtcccagcg cacatgttcg gcgaggcggg gcctgcgagc gcggccaccg agaatcggac    2640
gggggtagtc tcaagctggc cggcctgctc tggtgcctgg tctcgcgccg ccgtgtatcg    2700
ccccgccctg ggcggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt ttttttcttc    3120
catttcaggt gtcgtgacaa gtttgtacaa aaaagcaggc tgccaccatg ctcttgctcg    3180
tcacctcctt gctgctgtgt gaactgccgc accctgcgtt ccttcttatt ccacaggacc    3240
gacacatgat ccgaatgcgc caactcatag acatcgtaga ccagctcaag aattatgtca    3300
acgacctggt gcctgagttc ctcccggctc cagaggacgt cgaaacaaac tgcgaatggt    3360
ctgcttttag ctgttttcaa aaggcgcagt tgaaatcagc gaacacgggc aataatgagc    3420
gcattattaa cgtctcaatc aagaaactga aagaaagcc accgtcaaca aatgctgggc    3480
gacggcagaa acatagactt acctgcccaa gctgtgactc ctacgagaaa aagccgccga    3540
aagagtttct tgaaaggttc aagagcctcc tccagaaggt gtctaccctg agcttcatcg    3600
aatccaagta cggtcccca tgtccccgt gccccgcccc tgagtttctg ggggtccttt    3660
cagttttct gttcccgcca aagccaaagg acactctgat gatatccaga acaccggagg    3720
ttacttgtgt cgtggtcgat gttagccaag aggacccga agttcagttc aactggtatg    3780
tcgacggcgt ggaagtccat aatgcaaaaa cgaaaccacg ggaagagcaa ttcaatagca    3840
cctacagagt agtatcagtt ctgaccgttc tgcatcaaga ctggctcaac ggtaaagaat    3900
acaagtgcaa agtgtctaat aaaggcttgc ctagttccat agaaaagacc atcagcaagg    3960
cgaaagggca accacgagag ccacaagtct atacgcttcc cccatcacaa gaagaaatga    4020
cgaagaacca agtgagcttg acgtgcttgg tgaagggttt ttacccgtca gacatagccg    4080
tcgagtggga atcaaatggc cagcccgaga acaattacaa aacaactcca cccgttctcg    4140
actccgacgg ttccttttc ctctactcac gattgactgt agataagagc agatggcaag    4200
agggaaatgt gttctcttgt agcgtgatgc acgaagcact ccataaccac tacactcaga    4260
aatcactctc tctcagtctt gggaaaatgg cactcattgt gctcggtggg gtggcaggtc    4320
ttcttctgtt tattggcctt ggaatatttt tcgcccagct ttcttgtaca aagtggtgat    4380
aatcgaattc cgataatcaa cctctggatt acaaaatttg tgaaagattg actggtattc    4440
ttaactatgt tgctcctttt acgctatgtg gatacgctgc tttaatgcct ttgtatcatg    4500
```

```
ctattgcttc ccgtatggct ttcattttct cctccttgta taaatcctgg ttgctgtctc    4560
tttatgagga gttgtggccc gttgtcaggc aacgtggcgt ggtgtgcact gtgtttgctg    4620
acgcaacccc cactggttgg ggcattgcca ccacctgtca gctcctttcc gggactttcg    4680 cttccccct ccctattgcc acggcggaac tcatcgccgc ctgccttgcc cgctgctgga     4740
caggggctcg gctgttgggc actgacaatt ccgtggtgtt gtcggggaag ctgacgtcct    4800
ttccatggct gctcgcctgt gttgccacct ggattctgcg cggacgtcc ttctgctacg     4860 tcccttcggc cctcaatcca gcggaccttc cttcccgcgg cctgctgccg gctctgcggc    4920
ctcttccgcg tcttcgcctt cgccctcaga cgagtcggat ctcccttttgg gccgcctccc   4980 cgcatcggga attcccgcgg ttcgaattct accgggtagg ggaggcgctt ttcccaaggc    5040
agtctggagc atgcgcttta gcagccccgc tgggcacttg gcgctacaca agtgcctct    5100 ggcctcgcac acattccaca tccaccggta ggcgccaacc ggctccgttc tttggtggcc    5160
ccttcgcgcc accttctact cctcccctag tcaggaagtt ccccccccgcc ccgcagctcg   5220 cgtcgtgcag gacgtgacaa atggaagtag cacgtctcac tagtctcgtg cagatggaca   5280
gcaccgctga gcaatggaag cgggtaggcc tttggggcag cggccaatag cagctttgct   5340
ccttcgcttt ctgggctcag aggctgggaa ggggtgggtc cggggcggg ctcaggggcg    5400 ggctcagggg cggggcgggc gcccgaaggt cctccggagg cccggcattc tgcacgcttc    5460
aaaagcgcac gtctgccgcg ctgttctcct cttcctcatc tccgggcctt tcgacctcac    5520
gtggccacca tgaccgagta caagcccacg gtgcgcctcg ccacccgcga cgacgtcccc    5580
agggccgtac gcaccctcgc cgccgcgttc gccgactacc ccgccacgcg ccacaccgtc    5640
gatccggacc gccacatcga gcgggtcacc gagctgcaag aactcttcct cacgcgcgtc    5700
gggctcgaca tcggcaaggt gtgggtcgcg gacgacggcg ccgcggtggc ggtctggacc    5760
acgccggaga gcgtcgaagc gggggcgtg ttcgccgaga tcggcccgcg catggccgag    5820
ttgagcggtt cccggctggc cgcgcagcaa cagatggaag gcctcctggc gccgcaccgg    5880
cccaaggagc ccgcgtggtt cctgccacc gtcggcgtct cgcccgacca ccagggcaag    5940
ggtctgggca gcgccgtcgt gctccccgga gtggaggcgg ccgagcgcgc cggggtgccc    6000
gccttcctgg agacctccgc gccccgcaac ctcccccttct acgagcggct cggcttcacc    6060
gtcaccgccg acgtcgaggt gcccgaagga ccgcgcacct ggtgcatgac ccgcaagccc    6120
ggtgcctgag gtacctttaa gaccaatgac ttacaaggca gctgtagatc ttagccactt    6180
tttaaaagaa aaggggggac tggaagggct aattcactcc caacgaagac aagatctgct    6240
ttttgcttgt actgggtctc tctggttaga ccagatctga gcctgggagc tctctggcta    6300
actagggaac ccactgctta agcctcaata aagcttgcct tgagtgcttc aagtagtgtg    6360
tgcccgtctg ttgtgtgact ctggtaacta gagatccctc agacccttt agtcagtgtg    6420 gaaaatctct agcagtagta gttcatgtca tcttattatt cagtatttat aacttgcaaa    6480
gaaatgaata tcagagagtg agaggaactt gtttattgca gcttataatg gttacaaata   6540
aagcaatagc atcacaaatt tcacaaataa agcattttt tcactgcatt ctagttgtgg    6600
tttgtccaaa ctcatcaatg tatcttatca tgtctggctc tagctatccc gcccctaact    6660
ccgcccatcc cgcccctaac tccgcccagt tccgcccatt ctccgcccca tggctgacta    6720
atttttttta tttatgcaga ggccgaggcc gcctcggcct ctgagctatt ccagaagtag    6780
tgaggaggct ttttttggagg cctagggacg tacccaattc gccctatagt gagtcgtatt   6840
```

```
acgcgcgctc actggccgtc gttttacaac gtcgtgactg ggaaaaccct ggcgttaccc    6900
aacttaatcg ccttgcagca catcccccctt tcgccagctg gcgtaatagc gaagaggccc    6960
gcaccgatcg cccttcccaa cagttgcgca gcctgaatgg cgaatgggac gcgccctgta    7020
gcggcgcatt aagcgcggcg ggtgtggtgg ttacgcgcag cgtgaccgct acacttgcca    7080
gcgccctagc gcccgctcct ttcgctttct tcccttcctt tctcgccacg ttcgccggct    7140
ttccccgtca agctctaaat cggggggctcc ctttagggtt ccgatttagt gctttacggc    7200
acctcgaccc caaaaaactt gattagggtg atggttcacg tagtgggcca tcgccctgat    7260
agacggtttt tcgccctttg acgttggagt ccacgttctt taatagtgga ctcttgttcc    7320
aaactggaac aacactcaac cctatctcgg tctattcttt tgatttataa gggattttgc    7380
cgatttcggc ctattggtta aaaaatgagc tgatttaaca aaaatttaac gcgaatttta    7440
acaaaatatt aacgcttaca atttaggtgg cacttttcgg ggaaatgtgc gcggaacccc    7500
tatttgttta ttttcctaaa tacattcaaa tatgtatccg ctcatgagac aataaccctg    7560
ataaatgctt caataatatt gaaaaaggaa gagtatgagt attcaacatt tccgtgtcgc    7620
ccttattccc ttttttgcgg cattttgcct tcctgttttt gctcacccag aaacgctggt    7680
gaaagtaaaa gatgctgaag atcagttggg tgcacgagtg ggttacatcg aactggatct    7740
caacagcggt aagatccttg agagttttcg ccccgaagaa cgttttccaa tgatgagcac    7800
ttttaaagtt ctgctatgtg gcgcggtatt atcccgtatt gacgccgggc aagagcaact    7860
cggtcgccgc atacactatt ctcagaatga cttggttgag tactcaccag tcacagaaaa    7920
gcatcttacg gatggcatga cagtaagaga attatgcagt gctgccataa ccatgagtga    7980
taacactgcg gccaacttac ttctgacaac gatcggagga ccgaaggagc taaccgcttt    8040
tttgcacaac atgggggatc atgtaactcg ccttgatcgt tgggaaccgg agctgaatga    8100
agccatacca aacgacgagc gtgacaccac gatgcctgta gcaatggcaa caacgttgcg    8160
caaactatta actggcgaac tacttactct agcttcccgg caacaattaa tagactggat    8220
ggaggcggat aaagttgcag gaccacttct gcgctcggcc cttccggctg gctggtttat    8280
tgctgataaa tctggagccg gtgagcgtgg gtctcgcggt atcattgcag cactggggcc    8340
agatggtaag ccctcccgta tcgtagttat ctacacgacg gggagtcagg caactatgga    8400
tgaacgaaat agacagatcg ctgagatagg tgcctcactg attaagcatt ggtaactgtc    8460
agaccaagtt tactcatata ctttagat tgatttaaaa cttcattttt aatttaaaag    8520
gatctaggtg aagatccttt ttgataatct catgaccaaa atcccttaac gtgagttttc    8580
gttccactga gcgtcagacc ccgtagaaaa gatcaaagga tcttcttgag atcctttttt    8640
tctgcgcgta atctgctgct tgcaaacaaa aaaaccaccg ctaccagcgg tggtttgttt    8700
gccggatcaa gagctaccaa ctctttttcc gaaggtaact ggcttcagca gagcgcagat    8760
accaaatact gttcttctag tgtagccgta gttaggccac cacttcaaga actctgtagc    8820
accgcctaca tacctcgctc tgctaatcct gttaccagtg gctgctgcca gtggcgataa    8880
gtcgtgtctt accgggttgg actcaagacg atagttaccg gataaggcgc agcggtcggg    8940
ctgaacgggg ggttcgtgca cacagcccag cttggagcga acgacctaca ccgaactgag    9000
atacctacag cgtgagctat gagaaagcgc cacgcttccc gaagagagaa aggcggacag    9060
gtatccggta agcggcaggg tcggaacagg agagcgcacg agggagcttc caggggggaaa    9120 cgcctggtat ctttatagtc ctgtcgggtt tcgccacctc tgacttgagc gtcgattttt    9180
gtgatgctcg tcaggggggc ggagcctatg gaaaaacgcc agcaacgcgg cctttttacg    9240
```

```
gttcctggcc ttttgctggc cttttgctca catgttcttt cctgcgttat cccctgattc      9300
tgtggataac cgtattaccg cctttgagtg agctgatacc gctcgccgca gccgaacgac      9360
cgagcgcagc gagtcagtga gcgaggaagc ggaagagcgc ccaatacgca aaccgcctct      9420
ccccgcgcgt tggccgattc attaatgcag ctggcacgac aggtttcccg actggaaagc      9480
gggcagtgag cgcaacgcaa ttaatgtgag ttagctcact cattaggcac cccaggcttt      9540
acactttatg cttccggctc gtatgttgtg tggaattgtg agcggataac aatttcacac      9600
aggaaacagc tatgaccatg attacgccaa gcgcgcaatt aaccctcact aaagggaaca      9660
aaagctggag ctgcaagctt                                                  9680

<210> SEQ ID NO 6
<211> LENGTH: 9652
<212> TYPE: DNA
<213> ORGANISM: Artificial Sequence
<220> FEATURE:
<223> OTHER INFORMATION: Synthetic construct

<400> SEQUENCE: 6
aatgtagtct tatgcaatac tcttgtagtc ttgcaacatg gtaacgatga gttagcaaca        60
tgccttacaa ggagagaaaa agcaccgtgc atgccgattg gtggaagtaa ggtggtacga       120
tcgtgcctta ttaggaaggc aacagacggg tctgacatgg attggacgaa ccactgaatt       180 ccgcattgc agagatattg tatttaagtg cctagctcga tacataaacg ggtctctctg        240
gttagaccag atctgagcct gggagctctc tggctaacta gggaacccac tgcttaagcc       300
tcaataaagc ttgccttgag tgcttcaagt agtgtgtgcc cgtctgttgt gtgactctgg       360
taactagaga tccctcagac ccttttagtc agtgtggaaa atctctagca gtggcgcccg       420
aacagggact tgaaagcgaa agggaaacca gaggagctct ctcgacgcag gactcggctt       480
gctgaagcgc gcacggcaag aggcgagggg cggcgactgg tgagtacgcc aaaaattttg       540
actagcggag gctagaagga gagagatggg tgcgagagcg tcagtattaa gcgggggaga       600
attagatcgc gatgggaaaa aattcggtta aggccagggg gaagaaaaa atataaatta       660 aaacatatag tatgggcaag cagggagcta gaacgattcg cagttaatcc tggcctgtta       720
gaaacatcag aaggctgtag acaaatactg ggacagctac aaccatccct tcagacagga       780
tcagaagaac ttagatcatt atataataca gtagcaaccc tctattgtgt gcatcaaagg       840
atagagataa aagacaccaa ggaagcttta gacaagatag aggaagagca aaacaaaagt       900
aagaccaccg cacagcaagc ggccgctgat cttcagacct ggaggaggag atatgaggga       960
caattggaga agtgaattat ataaatataa agtagtaaaa attgaaccat taggagtagc      1020
acccaccaag gcaaagagaa gagtggtgca gagagaaaaa agagcagtgg aataggagc      1080 tttgttcctt gggttcttgg gagcagcagg aagcactatg ggcgcagcgt caatgacgct      1140
gacggtacag gccagacaat tattgtctgg tatagtgcag cagcagaaca atttgctgag      1200
ggctattgag gcgcaacagc atctgttgca actcacagtc tggggcatca agcagctcca      1260
ggcaagaatc ctggctgtgg aaagatacct aaaggatcaa cagctcctgg ggatttgggg      1320
ttgctctgga aaactcattt gcaccactgc tgtgccttgg aatgctagtt ggagtaataa      1380
atctctggaa cagatttgga atcacacgac ctggatggag tgggacagag aaattaacaa      1440
ttacacaagc ttaatacact ccttaattga agaatcgcaa aaccagcaag aaaagaatga      1500
acaagaatta ttggaattag ataaatgggc aagtttgtgg aattggttta acataacaaa      1560
```

-continued

```
ttggctgtgg tatataaaat tattcataat gatagtagga ggcttggtag gtttaagaat    1620 agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaaagaat agtagacata    1860
atagcaacag acatacaaac taagaattca caaaaacaaa ttacaaaaat tcaaaatttt    1920
actagtgatt atcggatcaa cttttgtatag aaaagttggg ctccggtgcc cgtcagtggg    1980
cagagcgcac atcgcccaca gtccccgaga agttgggggg aggggtcggc aattgaaccg    2040
gtgcctagag aaggtggcgc ggggtaaact gggaaagtga tgtcgtgtac tggctccgcc    2100 ttttcccga gggtggggga gaaccgtata taagtgcagt agtcgccgtg aacgttcttt    2160
ttcgcaacgg gtttgccgcc agaacacagg taagtgccgt gtgtggttcc cgcgggcctg    2220
gcctctttac gggttatggc ccttgcgtgc cttgaattac ttccacctgg ctgcagtacg    2280
tgattcttga tcccgagctt cgggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtgcacctt cgcgcctgtc tcgctgcttt cgataagtct ctagccattt    2460 aaaattttg atgacctgct gcgacgcttt ttttctggca agatagtctt gtaaatgcgg    2520
gccaagatct gcacactggt atttcggttt ttggggccgc gggcggcgac ggggcccgtg    2580
cgtcccagcg cacatgttcg gcgaggcggg gcctgcgagc gcggccaccg agaatcggac    2640
gggggtagtc tcaagctggc cggcctgctc tggtgcctgg tctcgcgccg ccgtgtatcg    2700
ccccgccctg ggcggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg ccttttcgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt tttttcttc    3120 catttcaggt gtcgtgacaa gtttgtacaa aaaagcaggc atgctgcttc tcgtaacgtc    3180
cttgttgttg tgcgaattgc ctcatccagc attcttgctt attcccaact gggtcaacgt    3240
aataagtgac ttgaaaaaaa tcgaggatct gatacagagt atgcacatcg atgcaacact    3300
ctacactgag agtgatgttc acccgagttg taaagtgaca gcgatgaaat gttttcttct    3360
tgaacttcag gttatatcac ttgaatcagg tgatgctagt atccatgaca cggtggagaa    3420
tctcatcatt cttgctaata acagtctctc ctcaaatggt aatgtaacag aatctggctg    3480
taaagaatgc gaggaattgg aggagaagaa cataaaggaa tttctccaga gcttcgtcca    3540
tatagtacag atgttcatca acacatccga gtctaaatac ggcccgccgt gtccaccgtg    3600
tccagcgcca gagtttctcg gtggcccttc tgtgttcctg ttcccccca gcccaaaga    3660 tacccttatg atatcaagaa caccagaagt cacttgtgtc gttgtcgatg tgagccaaga    3720
agaccctgag gtacagttca actggtatgt agatggggtt gaggttcata cgccaaaac    3780 taagcccaga gaagaacaat tcaatagtac ttatagagtt gtctcagtac ttacggtctt    3840
gcatcaagat tggttgaatg gtaaggaata taagtgcaaa gtgtccaata agggcctgcc    3900
aagcagtata gagaagacta ctctccaaggc aaaagggcaa ccccgcgaac cacaggtcta    3960
```

```
tactcttcca cccagccaag aggaaatgac taaaaatcaa gtatctctta cgtgccttgt    4020
gaaaggtttt tacccgagtg atattgccgt agagtgggaa tccaacggcc agccagagaa    4080
caactataag actacgccgc cggttttgga tagtgacggc tccttctttc tgtactccag    4140
gctcacggtc gacaagagtc gatggcaaga ggggaacgta tttagttgct ctgtgatgca    4200
tgaagcgctg cacaatcatt atactcagaa gagtctgtcc ctgagtctcg gcaaaatggc    4260
cctgattgta ctggggagggg ttgctggact tctcctgttt atcggactcg gtatcttctt    4320
ctgaacccag cttt cttgta caaagtggtg ataatcgaat tccgataatc aacctctgga    4380
ttacaaaatt tgtgaaagat tgactggtat tcttaactat gttgctccct ttacgctatg    4440
tggatacgct gctttaatgc ctttgtatca tgctattgct tcccgtatgg ctttcatttt    4500
ctcctccttg tataaatcct ggttgctgtc tctttatgag gagttgtggc ccgttgtcag    4560
gcaacgtggc gtggtgtgca ctgtgtttgc tgacgcaacc cccactggtt ggggcattgc    4620
caccacctgt cagctccttt ccgggacttt cgctttcccc ctccctattg ccacggcgga    4680
actcatcgcc gcctgccttg cccgctgctg gacaggggct cggctgttgg gcactgacaa    4740
ttccgtggtg ttgtcgggga agctgacgtc cttt ccatgg ctgctcgcct gtgttgccac    4800
ctggattctg cgcgggacgt cctt ctgcta cgtcccttcg gccctcaatc cagcggacct    4860
tccttcccgc ggcctgctgc cggctctgcg gcctcttccg cgtcttcgcc ttcgccctca    4920
gacgagtcgg atctccctt t gggccgcctc cccgcatcgg gaattcccgc ggttcgaatt    4980
ctaccgggta ggggaggcgc ttttcccaag gcagtctgga gcatgcgctt tagcagcccc    5040
gctgggcact tggcgctaca caagtggcct ctggcctcgc acacattcca catccaccgg    5100
taggcgccaa ccggctccgt tctttggtgg ccccttcgcg ccaccttcta ctcctcccct    5160
agtcaggaag ttccccccccg ccccgcagct cgcgtcgtgc aggacgtgac aaatggaagt    5220
agcacgtctc actagtctcg tgcagatgga cagcaccgct gagcaatgga agcgggtagg    5280 cctttgggc agcggccaat agcagctttg ctccttcgct ttctgggctc agaggctggg    5340 aagggggtggg tccggggggcg ggctcagggg cgggctcagg ggcggggcgg gcgcccgaag    5400
gtcctccgga ggcccggcat tctgcacgct tcaaaagcgc acgtctgccg cgctgttctc    5460
ctcttcctca tctccgggcc tttcgacctc acgtggccac catgaccgag tacaagccca    5520
cggtgcgcct cgccacccgc gacgacgtcc ccagggccgt acgcaccctc gccgccgcgt    5580
tcgccgacta ccccgccacg cgccacaccg tcgatccgga ccgccacatc gagcgggtca    5640
ccgagctgca agaactcttc ctcacgcgcg tcgggctcga catcggcaag gtgtgggtcg    5700
cggacgacgg cgccgcggtg gcggtctgga ccacgccgga gagcgtcgaa gcggggcgg    5760 tgttcgccga gatcggcccg cgcatggccg agttgagcgg ttcccggctg gccgcgcagc    5820
aacagatgga aggcctcctg gcgccgcacc ggcccaagga gcccgcgtgg ttcctggcca    5880
ccgtcggcgt ctcgcccgac caccagggca agggtctggg cagcgccgtc gtgctccccg    5940
gagtggaggc ggccgagcgc gccggggtgc ccgccttcct ggagacctcc gcgccccgca    6000
acctcccctt ctacgagcgg ctcggcttca ccgtcaccgc cgacgtcgag gtgcccgaag    6060
gaccgcgcac ctggtgcatg acccgcaagc ccggtgcctg aggtaccttt aagaccaatg    6120
acttacaagg cagctgtaga tcttagccac ttttttaaaag aaaaggggggg actggaaggg    6180 ctaattcact cccaacgaag acaagatctg ctttttgctt gtactgggtc tctctggtta    6240
gaccagatct gagcctggga gctctctggc taactaggga acccactgct taagcctcaa    6300
```

```
taaagcttgc cttgagtgct tcaagtagtg tgtgcccgtc tgttgtgtga ctctggtaac    6360
tagagatccc tcagaccctt ttagtcagtg tggaaaatct ctagcagtag tagttcatgt    6420
catcttatta ttcagtattt ataacttgca agaaatgaa tatcagagag tgagaggaac    6480
ttgtttattg cagcttataa tggttacaaa taaagcaata gcatcacaaa tttcacaaat    6540
aaagcatttt tttcactgca ttctagttgt ggtttgtcca aactcatcaa tgtatcttat    6600
catgtctggc tctagctatc ccgcccctaa ctccgcccat cccgcccta actccgccca    6660
gttccgccca ttctccgccc catggctgac taatttttt tatttatgca gaggccgagg    6720
ccgcctcggc ctctgagcta ttccagaagt agtgaggagg cttttttgga ggcctaggga    6780
cgtacccaat tcgccctata gtgagtcgta ttacgcgcgc tcactggccg tcgttttaca    6840
acgtcgtgac tgggaaaacc ctggcgttac ccaacttaat cgccttgcag cacatccccc    6900
tttcgccagc tggcgtaata gcgaagaggc ccgcaccgat cgcccttccc aacagttgcg    6960
cagcctgaat ggcgaatggg acgcgccctg tagcggcgca ttaagcgcgg cgggtgtggt    7020
ggttacgcgc agcgtgaccg ctacacttgc cagcgcccta gcgcccgctc ctttcgcttt    7080
cttcccttcc tttctcgcca cgttcgccgg ctttccccgt caagctctaa atcggggct    7140
ccctttaggg ttccgattta gtgctttacg gcacctcgac cccaaaaaac ttgattaggg    7200
tgatggttca cgtagtgggc catcgccctg atagacggtt tttcgccctt gacgttgga    7260
gtccacgttc tttaatagtg gactcttgtt ccaaactgga acaacactca accctatctc    7320
ggtctattct tttgatttat aagggatttt gccgatttcg gcctattggt taaaaaatga    7380
gctgatttaa caaaaattta acgcgaattt taacaaaata ttaacgctta caatttaggt    7440
ggcacttttc ggggaaatgt gcgcggaacc cctatttgtt tatttttcta aatacattca    7500
aatatgtatc cgctcatgag acaataaccc tgataaatgc ttcaataata ttgaaaaagg    7560
aagagtatga gtattcaaca tttccgtgtc gcccttattc ccttttttgc ggcattttgc    7620
cttcctgttt ttgctcaccc agaaacgctg gtgaaagtaa aagatgctga agatcagttg    7680
ggtgcacgag tgggttacat cgaactggat ctcaacagcg gtaagatcct tgagagtttt    7740
cgccccgaag aacgttttcc aatgatgagc acttttaaag ttctgctatg tggcgcggta    7800
ttatcccgta ttgacgccgg gcaagagcaa ctcggtcgcc gcatacacta ttctcagaat    7860
gacttggttg agtactcacc agtcacagaa aagcatctta cggatggcat gacagtaaga    7920
gaattatgca gtgctgccat aaccatgagt gataacactg cggccaactt acttctgaca    7980
acgatcggag gaccgaagga gctaaccgct tttttgcaca acatgggga tcatgtaact    8040
cgccttgatc gttgggaacc ggagctgaat gaagccatac caaacgacga gcgtgacacc    8100
acgatgcctg tagcaatggc aacaacgttg cgcaaactat taactggcga actacttact    8160
ctagcttccc ggcaacaatt aatagactgg atggaggcgg ataaagttgc aggaccactt    8220
ctgcgctcgg cccttccggc tggctggttt attgctgata atctggagc cggtgagcgt    8280
gggtctcgcg gtatcattgc agcactgggg ccagatggta agccctcccg tatcgtagtt    8340
atctacacga cggggagtca ggcaactatg gatgaacgaa atagacagat cgctgagata    8400
ggtgcctcac tgattaagca ttggtaactg tcagaccaag tttactcata tactttag    8460
attgatttaa aacttcattt ttaatttaaa aggatctagg tgaagatcct ttttgataat    8520
ctcatgacca aaatccctta acgtgagttt tcgttccact gagcgtcaga ccccgtagaa    8580
aagatcaaag gatcttcttg agatcctttt tttctgcgcg taatctgctg cttgcaaaca    8640
aaaaaaccac cgctaccagc ggtggtttgt ttgccggatc aagagctacc aactctttt    8700
```

```
ccgaaggtaa ctggcttcag cagagcgcag ataccaaata ctgttcttct agtgtagccg    8760
tagttaggcc accacttcaa gaactctgta gcaccgccta catacctcgc tctgctaatc    8820
ctgttaccag tggctgctgc cagtggcgat aagtcgtgtc ttaccgggtt ggactcaaga    8880
cgatagttac cggataaggc gcagcggtcg ggctgaacgg ggggttcgtg cacacagccc    8940
agcttggagc gaacgaccta caccgaactg agatacctac agcgtgagct atgagaaagc    9000
gccacgcttc ccgaagagag aaaggcggac aggtatccgg taagcggcag ggtcggaaca    9060
ggagagcgca cgagggagct tccaggggga aacgcctggt atctttatag tcctgtcggg    9120
tttcgccacc tctgacttga gcgtcgattt ttgtgatgct cgtcaggggg cggagccta    9180 tggaaaaacg ccagcaacgc ggcctttta cggttcctgg ccttttgctg gccttttgct    9240
cacatgttct ttcctgcgtt atcccctgat tctgtggata accgtattac cgcctttgag    9300
tgagctgata ccgctcgccg cagccgaacg accgagcgca gcgagtcagt gagcgaggaa    9360
gcggaagagc gcccaatacg caaaccgcct ctccccgcgc gttggccgat tcattaatgc    9420
agctggcacg acaggtttcc cgactggaaa gcgggcagtg agcgcaacgc aattaatgtg    9480
agttagctca ctcattaggc accccaggct ttacacttta tgcttccggc tcgtatgttg    9540
tgtggaattg tgagcggata caatttcac acaggaaaca gctatgacca tgattacgcc    9600
aagcgcgcaa ttaaccctca ctaaagggaa caaaagctgg agctgcaagc tt           9652

<210> SEQ ID NO 7
<211> LENGTH: 10907
<212> TYPE: DNA
<213> ORGANISM: Artificial Sequence
<220> FEATURE:
<223> OTHER INFORMATION: Synthetic construct

<400> SEQUENCE: 7
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
```

```
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaagaat agtagacata    1860 atagcaacag acatcaaac taaagaatta caaaaacaaa ttacaaaaat tcaaaatttt    1920
actagtgatt atcggatcaa cttttgtatag aaaagttggg ctccggtgcc cgtcagtggg    1980
cagagcgcac atcgcccaca gtccccgaga agttgggggg aggggtcggc aattgaaccg    2040
gtgcctagaa aaggtggcgc ggggtaaact gggaaagtga tgtcgtgtac tggctccgcc    2100
tttttcccga gggtggggga gaaccgtata taagtgcagt agtcgccgtg aacgttcttt    2160
ttcgcaacgg gtttgccgcc agaacacagg taagtgccgt gtgtggttcc cgcgggcctg    2220
gcctctttac gggttatggc ccttgcgtgc cttgaattac ttccacctgg ctgcagtacg    2280
tgattcttga tcccgagctt cggggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtggcacctt cgcgcctgtc tcgctgctt cgataagtct ctagccattt    2460 aaaattttg atgacctgct gcgacgcttt ttttctggca agatagtctt gtaaatgcgg    2520
gccaagatct gcacactggt atttcggttt ttggggccgc gggcggcgac ggggcccgtg    2580
cgtcccagcg cacatgttcg gcgaggcggg gcctgcgagc gcggccaccg agaatcggac    2640
gggggtagtc tcaagctggc cggcctgctc tggtgcctgg tctcgcgccg ccgtgtatcg    2700
ccccgccctg ggcggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt ttttttcttc    3120
catttcaggt gtcgtgacaa gtttgtacaa aaaagcaggc tgccaccatg ctcttgctcg    3180
tcacctcctt gctgctgtgt gaactgccgc accctgcgtt ccttcttatt ccacaggacc    3240
gacacatgat ccgaatgcgc caactcatag acatcgtaga ccagctcaag aattatgtca    3300
acgacctggt gcctgagttc ctcccggctc cagaggacgt cgaaacaaac tgcgaatggt    3360 ctgctttttag ctgttttcaa aaggcgcagt tgaaatcagc gaacacgggc aataatgagc    3420
gcattattaa cgtctcaatc aagaaactga aaagaaagcc accgtcaaca aatgctgggc    3480
```

```
gacggcagaa acatagactt acctgcccaa gctgtgactc ctacgagaaa aagccgccga    3540
aagagtttct tgaaaggttc aagagcctcc tccagaaggt gtctaccctg agcttcatcg    3600
aatccaagta cggtccccca tgtccccgt gccccgcccc tgagtttctg ggggtccttt    3660 cagttttttct gttcccgcca aagccaaagg acactctgat gatatccaga acaccggagg   3720
ttacttgtgt cgtggtcgat gttagccaag aggaccccga agttcagttc aactggtatg    3780
tcgacggcgt ggaagtccat aatgcaaaaa cgaaaccacg ggaagagcaa ttcaatagca    3840
cctacagagt agtatcagtt ctgaccgttc tgcatcaaga ctggctcaac ggtaaagaat    3900
acaagtgcaa agtgtctaat aaaggcttgc ctagttccat agaaaagacc atcagcaagg    3960
cgaaagggca accacgagag ccacaagtct atacgcttcc cccatcacaa gaagaaatga    4020
cgaagaacca agtgagcttg acgtgcttgg tgaagggttt ttacccgtca gacatagccg    4080
tcgagtggga atcaaatggc cagcccgaga acaattacaa aacaactcca cccgttctcg    4140
actccgacgg ttcctttttc ctctactcac gattgactgt agataagagc agatggcaag    4200
agggaaatgt gttctcttgt agcgtgatgc acgaagcact ccataaccac tacactcaga    4260
aatcactctc tctcagtctt gggaaaatgg cactcattgt gctcggtggg gtggcaggtc    4320
ttcttctgtt tattggcctt ggaatatttt tcggaagcgg agagggcagg ggaagtcttc    4380
taacatgcgg ggacgtggag gaaaatcccg gccccatgct gcttctcgta acgtccttgt    4440
tgttgtgcga attgcctcat ccagcattct tgcttattcc caactgggtc aacgtaataa    4500
gtgacttgaa aaaatcgag gatctgatac agagtatgca catcgatgca acactctaca    4560
ctgagagtga tgttcacccg agttgtaaag tgacagcgat gaaatgtttt cttcttgaac    4620
ttcaggttat atcacttgaa tcaggtgatg ctagtatcca tgacacggtg gagaatctca    4680
tcattcttgc taataacagt ctctcctcaa atggtaatgt aacagaatct ggctgtaaag    4740
aatgcgagga attggaggag aagaacataa aggaatttct ccagagcttc gtccatatag    4800
tacagatgtt catcaacaca tccgagtcta aatacggccc gccgtgtcca ccgtgtccag    4860
cgccagagtt tctcggtggc ccttctgtgt tcctgttccc cccaagccc aaagatacccc    4920 ttatgatatc aagaacacca gaagtcactt gtgtcgttgt cgatgtgagc caagaagacc    4980
ctgaggtaca gttcaactgg tatgtagatg gggttgaggt tcataacgcc aaaactaagc    5040
ccagagaaga acaattcaat agtacttata gagttgtctc agtacttacg gtcttgcatc    5100
aagattggtt gaatggtaag gaatataagt gcaaagtgtc caataagggc ctgccaagca    5160
gtatagaaga gactatctcc aaggcaaaag ggcaaccccg cgaaccacag gtctatactc    5220
ttccacccag ccaagaggaa atgactaaaa atcaagtatc tcttacgtgc cttgtgaaag    5280
gtttttaccc gagtgatatt gccgtagagt gggaatccaa cggccagcca gagaacaact    5340
ataagactac gccgccggtt ttggatagtg acggctcctt cttctgtac tccaggctca    5400 cggtcgacaa gagtcgatgg caagagggga acgtatttag ttgctctgtg atgcatgaag    5460
cgctgcacaa tcattatact cagaagagtc tgtccctgag tctcggcaaa atggccctga    5520
ttgtactggg aggggttgct ggacttctcc tgtttatcgg actcggtatc ttcttctgaa    5580
cccagctttc ttgtacaaag tggtgataat cgaattccga taatcaacct ctggattaca    5640
aaatttgtga agattgact ggtattctta actatgttgc tccttttacg ctatgtggat    5700
acgctgcttt aatgcctttg tatcatgcta ttgcttcccg tatggctttc attttctcct    5760
ccttgtataa atcctggttg ctgtctcttt atgaggagtt gtggcccgtt gtcaggcaac    5820
```

-continued

```
gtggcgtggt gtgcactgtg tttgctgacg caaccccccac tggttggggc attgccacca    5880
cctgtcagct cctttccggg actttcgctt tccccctccc tattgccacg gcggaactca    5940
tcgccgcctg ccttgcccgc tgctggacag gggctcggct gttgggcact gacaattccg    6000
tggtgttgtc ggggaagctg acgtcctttc catggctgct cgcctgtgtt gccacctgga    6060
ttctgcgcgg gacgtccttc tgctacgtcc cttcggccct caatccagcg gaccttcctt    6120
cccgcggcct gctgccggct ctgcggcctc ttccgcgtct tcgccttcgc cctcagacga    6180
gtcggatctc cctttgggcc gcctccccgc atcgggaatt cccgcggttc gaattctacc    6240
gggtagggga ggcgcttttc ccaaggcagt ctggagcatg cgctttagca gccccgctgg    6300
gcacttggcg ctacacaagt ggcctctggc ctcgcacaca ttccacatcc accggtaggc    6360
gccaaccggc tccgttcttt ggtgcccct tcgcgccacc ttctactcct cccctagtca    6420
ggaagttccc ccccgccccg cagctcgcgt cgtgcaggac gtgacaaatg gaagtagcac    6480
gtctcactag tctcgtgcag atggacagca ccgctgagca atggaagcgg gtaggccttt    6540
ggggcagcgg ccaatagcag ctttgctcct tcgcttctg gctcagagg ctgggaaggg    6600
gtgggtccgg gggcgggctc aggggcgggc tcaggggcgg ggcgggcgcc cgaaggtcct    6660
ccggaggccc ggcattctgc acgcttcaaa agcgcacgtc tgccgcgctg ttctcctctt    6720
cctcatctcc gggcctttcg acctcacgtg gccaccatga ccgagtacaa gcccacggtg    6780
cgcctcgcca cccgcgacga cgtccccagg gccgtacgca ccctcgccgc gcgttcgcc    6840
gactaccccg ccacgcgcca caccgtcgat ccggaccgcc acatcgagcg ggtcaccgag    6900
ctgcaagaac tcttcctcac gcgcgtcggg ctcgacatcg caaggtgtg ggtcgcggac    6960
gacggcgccg cggtggcggt ctggaccacg ccggagagcg tcgaagcggg ggcggtgttc    7020
gccgagatcg gcccgcgcat ggccgagttg agcggttccc ggctggccgc gcagcaacag    7080
atggaaggcc tcctggcgcc gcaccggccc aaggagcccg cgtggttcct ggccaccgtc    7140
ggcgtctcgc ccgaccacca gggcaagggt ctgggcagcg ccgtcgtgct ccccggagtg    7200
gaggcggccg agcgcgccgg ggtgcccgcc ttcctggaga cctccgcgcc ccgcaacctc    7260
cccttctacg agcggctcgg cttcaccgtc accgccgacg tcgaggtgcc cgaaggaccg    7320
cgcacctggt gcatgacccg caagcccggt gcctgaggta cctttaagac caatgactta    7380
caaggcagct gtagatctta gccacttttt aaaagaaaag gggggactgg aagggctaat    7440
tcactcccaa cgaagacaag atctgctttt tgcttgtact gggtctctct ggttagacca    7500
gatctgagcc tgggagctct ctggctaact agggaaccca ctgcttaagc ctcaataaag    7560
cttgccttga gtgcttcaag tagtgtgtgc ccgtctgttg tgtgactctg gtaactagag    7620
atccctcaga cccttttagt cagtgtggaa aatctctagc agtagtagtt catgtcatct    7680
tattattcag tatttataac ttgcaaagaa atgaatatca gagagtgaga ggaacttgtt    7740
tattgcagct tataatggtt acaaataaag caatagcatc acaaatttca caaataaagc    7800
atttttttca ctgcattcta gttgtggttt gtccaaactc atcaatgtat cttatcatgt    7860
ctggctctag ctatcccgcc cctaactccg cccatcccgc cctaactccg cccagttcc    7920
gcccattctc cgccccatgg ctgactaatt ttttattt atgcagaggc cgaggccgcc    7980
tcggcctctg agctattcca gaagtagtga ggaggctttt ttggaggcct agggacgtac    8040
ccaattcgcc ctatagtgag tcgtattacg cgcgctcact ggccgtcgtt ttacaacgtc    8100
gtgactggga aaaccctggc gttacccaac ttaatcgcct tgcagcacat ccccctttcg    8160
ccagctggcg taatagcgaa gaggcccgca ccgatcgccc ttcccaacag ttgcgcagcc    8220
```

-continued

```
tgaatggcga atgggacgcg ccctgtagcg gcgcattaag cgcggcgggt gtggtggtta    8280
cgcgcagcgt gaccgctaca cttgccagcg ccctagcgcc cgctcctttc gctttcttcc    8340
cttcctttct cgccacgttc gccggctttc cccgtcaagc tctaaatcgg gggctcccctt   8400 tagggttccg atttagtgct ttacggcacc tcgaccccaa aaaacttgat tagggtgatg    8460
gttcacgtag tgggccatcg ccctgataga cggttttcg ccctttgacg ttggagtcca     8520
cgttctttaa tagtggactc ttgttccaaa ctggaacaac actcaaccct atctcggtct    8580
attcttttga tttataaggg attttgccga tttcggccta ttggttaaaa aatgagctga    8640
tttaacaaaa atttaacgcg aattttaaca aaatattaac gcttacaatt taggtggcac    8700
ttttcgggga aatgtgcgcg gaacccctat ttgtttattt ttctaaatac attcaaatat    8760
gtatccgctc atgagacaat aaccctgata aatgcttcaa taatattgaa aaaggaagag    8820
tatgagtatt caacatttcc gtgtcgccct tattcccttt tttgcggcat tttgccttcc    8880 tgttttgct cacccagaaa cgctggtgaa agtaaaagat gctgaagatc agttgggtgc     8940
acgagtgggt tacatcgaac tggatctcaa cagcggtaag atccttgaga gttttcgccc    9000
cgaagaacgt tttccaatga tgagcacttt taaagttctg ctatgtggcg cggtattatc    9060
ccgtattgac gccgggcaag agcaactcgg tcgccgcata cactattctc agaatgactt    9120
ggttgagtac tcaccagtca cagaaaagca tcttacggat ggcatgacag taagagaatt    9180
atgcagtgct gccataacca tgagtgataa cactgcggcc aacttacttc tgacaacgat    9240
cggaggaccg aaggagctaa ccgcttttt gcacaacatg ggggatcatg taactcgcct     9300
tgatcgttgg gaaccggagc tgaatgaagc cataccaaac gacgagcgtg acaccacgat    9360
gcctgtagca atggcaacaa cgttgcgcaa actattaact ggcgaactac ttactctagc    9420
ttcccggcaa caattaatag actggatgga ggcggataaa gttgcaggac cacttctgcg    9480
ctcggccctt ccggctggct ggtttattgc tgataaatct ggagccggtg agcgtgggtc    9540
tcgcggtatc attgcagcac tggggccaga tggtaagccc tcccgtatcg tagttatcta    9600
cacgacgggg agtcaggcaa ctatggatga acgaaataga cagatcgctg agataggtgc    9660
ctcactgatt aagcattggt aactgtcaga ccaagtttac tcatatatac tttagattga    9720
tttaaaactt catttttaat ttaaaaggat ctaggtgaag atccttttg ataatctcat     9780 gaccaaaatc ccttaacgtg agttttcgtt ccactgagcg tcagaccccg tagaaaagat    9840
caaaggatct tcttgagatc cttttttct gcgcgtaatc tgctgcttgc aaacaaaaaa     9900
accaccgcta ccagcggtgg tttgtttgcc ggatcaagag ctaccaactc ttttttccgaa   9960 ggtaactggc ttcagcagag cgcagatacc aaatactgtt cttctagtgt agccgtagtt   10020
aggccaccac ttcaagaact ctgtagcacc gcctacatac ctcgctctgc taatcctgtt   10080
accagtggct gctgccagtg gcgataagtc gtgtcttacc gggttggact caagacgata   10140
gttaccggat aaggcgcagc ggtcgggctg aacggggggt tcgtgcacac agcccagctt   10200
ggagcgaacg acctacaccg aactgagata cctacagcgt gagctatgag aaagcgccac   10260
gcttcccgaa gagagaaagg cggacaggta tccggtaagc ggcagggtcg gaacaggaga   10320
gcgcacgagg gagcttccag ggggaaacgc ctggtatctt tatagtcctg tcgggtttcg   10380
ccacctctga cttgagcgtc gatttttgtg atgctcgtca ggggggcgga gcctatggaa   10440
aaacgccagc aacgcggcct ttttacggtt cctggccttt tgctggcctt ttgctcacat   10500
gttctttcct gcgttatccc ctgattctgt ggataaccgt attaccgcct ttgagtgagc   10560
```

```
tgataccgct cgccgcagcc gaacgaccga gcgcagcgag tcagtgagcg aggaagcgga    10620
agagcgccca atacgcaaac cgcctctccc cgcgcgttgg ccgattcatt aatgcagctg    10680
gcacgacagg tttcccgact ggaaagcggg cagtgagcgc aacgcaatta atgtgagtta    10740
gctcactcat taggcacccc aggctttaca ctttatgctt ccggctcgta tgttgtgtgg    10800
aattgtgagc ggataacaat ttcacacagg aaacagctat gaccatgatt acgccaagcg    10860
cgcaattaac cctcactaaa gggaacaaaa gctggagctg caagctt                  10907
```

COMPOSITIONS FOR EXPANDING NATURAL KILLER CELLS

RELATED APPLICATIONS

This application is a National Stage application of PCT international application PCT/US2018/033668, filed on May 21, 2018, which claims the benefit of U.S. Provisional Application No. 62/578,742 filed Oct. 30, 2017; U.S. Provisional Application No. 62/538,961 filed Jul. 31, 2017; and U.S. Provisional Application No. 62/508,666 filed May 19, 2018, all of which are hereby incorporated by reference in their entireties.

REFERENCE TO A SEQUENCE LISTING

The material in the ASCII text file, named "CASEU-57518WO-Sequences_ST25.txt", created May 21, 2018, file size of 53,248 bytes, is hereby incorporated by reference.

TECHNICAL FIELD

The disclosure relates generally to methods for expanding and enhancing the cytotoxic activity of natural killer cells to produce a large amount of highly active natural killer cells. The disclosure also relates to a genetically modified cell line for use as a feeder cell line for natural killer cell expansion. The disclosure further relates to methods of treating a variety of cancers using natural killer cells expanded by the disclosed methods.

BACKGROUND

A number of cancers are, at present, incurable. For others, chemotherapy is only partially effective and a significant proportion of patients relapse following treatment. Some haematological malignancies can be treated by hematopoietic stem cell transplantation (HSCT), but fewer than 30% of patients requiring HSCT have a suitable donor and are the requisite age. Thus, new strategies are required.

Natural killer (NK) cells are present in an amount of about 10-15% of white blood cells in the blood of normal people, and have high killing ability when they react with non-self material. Natural killer cells non-specifically and immediately act in response to the infection of cells with various viruses, the penetration of bacteria or the production of abnormal cells to thereby remove foreign matter. They kill malignant cells without antigen-specific receptor recognition. Cancer cells commonly upregulate ligands for NK cell activating receptors such as Major histocompatibility complex (MHC) class I chain-related protein A (MICA) and MHC class I chain-related protein (MICB) and downregulate ligands for inhibitory receptors such as HLA class I. In particular, cancer cells routinely downregulate HLA to avoid T-cell detection, making these cells paradoxically sensitive to NK cell killing. As normal cells express HLA class I (as well as lower levels of activating ligands), they are protected from NK cell-mediated killing. While T cell therapy, particularly chimeric antigen receptor therapy (CAR-T) has shown enormous promise for B cell malignancies, this strategy typically requires individual donor cells to be clinically manufactured for each patient, making it an extremely expensive process. These cells have also only shown significant clinical efficacy for a subset of patients with lymphoid leukemia to date. In addition, while allogeneic T cells cause severe graft-vs-host disease (GVHD), allogeneic NK cells have been found to be safe and do not cause GVHD in patients.

To date, three key obstacles have impeded the clinical use of NK cells, including: 1) lack of a robust ex vivo NK cell expansion system; 2) insufficient NK cell activity against tumor cells; and 3) maintenance and proliferation of NK cells in cancer patients despite a highly suppressive tumor microenvironment. For these reasons, methods for the proliferation and production of effective natural killer cells are required. Provided herein is a genetically manipulated feeder cell line (termed "NKF") that provides robust expansion of NK cells ex vivo. Also provided herein are methods for expanding and activating NK cells employing NKF cells. Further provided herein are methods of treating a cancer with NK cells produced by the novel expansion platform. In certain embodiments, the NK cells can be provided by a universal donor, abrogating the need for individualized therapy approaches.

SUMMARY

According to the present disclosure, in a first aspect, is a composition comprising acute myeloid leukemia (AML) cells engineered to express a membrane-bound interleukin (mbIL) protein.

In an example of the first aspect, the mbIL protein comprises a polypeptide sequence of SEQ ID NO: 1, SEQ ID NO:3, sequences having greater than 80% sequence homology with SEQ ID NO: 1, sequences having greater than 80% sequence homology with SEQ ID NO:3, or combinations thereof.

In another aspect of the first aspect, the mbIL protein comprises a polypeptide sequence of SEQ ID NO: 1 or sequences having greater than 80% sequence homology with SEQ ID NO:1.

In yet another example of the first aspect, the mbIL protein comprises a polypeptide sequence of SEQ ID NO:3 or sequences having greater than 80% sequence homology with SEQ ID NO:3.

In another example of the first aspect, the mbIL protein comprises a polypeptide sequence encoded by the nucleotide sequence of SEQ ID NO: 2 or SEQ ID NO:4.

In another example of the first aspect, the nucleotide sequence of SEQ ID NO:2 encodes the polypeptide of SEQ ID NO: 1.

In yet another example of the first aspect, the nucleotide sequence of SEQ ID NO:4 encodes the polypeptide of SEQ ID NO:2.

In another example of the first aspect, the AML cells are OCI-AML3 cells.

In yet another example of the first aspect, the cells are HL-60 cells.

In a second aspect, there is a method for expanding natural killer (NK) cells ex vivo, said method comprising harvesting donor cells from a donor subject; isolating the NK cells; and expanding the NK cells in the presence of OCI-AML3 feeder cells; or OCI-AML3 feeder cells and one or more of IL-2, IL-15, ALT-803, hetIL-15, IL-12, IL-18, IL-21 or derivatives or fragments thereof.

In an example of the second aspect, the OCI-AML3 feeder cells are engineered express to a membrane-bound interleukin (mbIL) protein.

In another example of the second aspect, the mbIL protein comprises a polypeptide sequence of SEQ ID NO: 1, SEQ ID NO:3, sequences having greater than 80% sequence homology with SEQ ID NO: 1, sequences having greater than 80% sequence homology with SEQ ID NO:3, or combinations thereof.

In an example of the second aspect, the NK cells are genetically modified to express one or proteins capable of providing cytokine support. In certain exemplary aspects, the proteins capable of providing cytokine support are selected from the group consisting of mbIL-15, soluble IL-15, soluble IL-21, mbIL-21, mbIL-2, or soluble IL-2.

In another aspect of the second embodiment, the NK cells are genetically modified to express one or proteins capable of inhibiting TGFβ signaling. In one exemplary aspect, the proteins capable of inhibiting TGFβ signaling is a dominant negative TGFβRII in which there is a truncation of the cytoplasmic domain.

In another example of the second aspect, the donor cells are autologous.

In another example of the second aspect, the donor cells are allogenic.

In yet another example of the second aspect, the donor cells are harvested from a living donor.

In another example of the second aspect, the donor cells are harvested from a cord blood.

In yet another example of the second aspect, a ratio of feeder cells:NK cells is at least 1:1 based on an amount of NK cells present at the time of refreshing.

In another example of the second aspect, the ratio of feeder cells:NK cells is about 5:1.

In yet another example of the second aspect, the ratio of feeder cells:NK cells is about 10:1.

In another example of the second aspect, the step of expanding the NK cells provides at least a 10,000-fold expansion within 4 weeks.

In another example of the second aspect, the step of expanding the NK cells provides at least a 20,000-fold expansion.

In yet another example of the second aspect, the step of expanding the NK cells provides at least a 30,000-fold expansion.

In another example of the second aspect, the step of expanding the NK cells continues for at least 4 weeks.

In another example of the second aspect, the step of expanding the NK cells continues for at least 6 weeks.

In yet another example of the second aspect, the feeder cells are refreshed weekly throughout the step of expanding the NK cells.

In a third aspect, there is a method of treating a recipient subject in need thereof, said method comprising: harvesting donor cells from a donor subject; isolating the natural killer (NK) cells; expanding the NK cells in the presence of OCI-AML3 feeder cells; or OCI-AML3 feeder cells and one or more of IL-2, IL-15, ALT-803, hetIL-15, IL-12, IL-18, IL-21 or derivatives or fragments thereof; and administering the expanded cells to the recipient subject.

In an example of the third aspect, the OCI-AML3 feeder cells are engineered express to a membrane-bound interleukin (mbIL) protein.

In another example of the third aspect, the mbIL protein comprises a polypeptide sequence of SEQ ID NO: 1, SEQ ID NO:3, sequences having greater than 90% sequence homology with SEQ ID NO: 1, sequences having greater than 90% sequence homology with SEQ ID NO:3, or combinations thereof.

In another example of the third embodiment, the NK cells are genetically modified to express one or proteins capable of providing cytokine support. In certain exemplary aspects, the proteins capable of providing cytokine support are selected from the group consisting of mbIL-15, soluble IL-15, soluble IL-21, mbIL-21, mbIL-2, or soluble IL-2.

In another aspect of the third embodiment, the NK cells are genetically modified to express one or more proteins capable of inhibiting TGFβ signaling. In one exemplary aspect, the proteins capable of inhibiting TGFβ signaling is dominant negative TGF-beta RII in where there is a truncation of the cytoplasmic domain.

In an example of the third aspect, the donor subject and the recipient subject are the same human.

In another example of the third aspect, the donor subject and the recipient subject are different humans.

In another example of the third aspect, the donor cells are harvested from cord blood.

In yet another example of the third aspect, the expanded cells are administered as monotherapy.

In another example of the third aspect, the expanded cells are administered concomitantly or sequentially with at least one additional therapeutic.

In another example of the third aspect, the at least one additional therapeutic is a cytokine support administered concomitantly.

In another example of the third aspect, the cytokine support is selected from the group consisting of IL-15, IL-2, ALT-803, IL-18, IL-12, IL-21 and derivatives and combinations thereof.

In another example of the third aspect, the additional therapeutic is IL-15 or a derivative thereof.

In yet another example of the third aspect, the at least one additional therapeutic is an inhibitor of an immunoregulatory protein.

In another example of the third aspect, the inhibitor of an immunoregulatory protein is selected from the group consisting of a TGF-beta inhibitor, a GSK3 inhibitor, a PD1 inhibitor, a PDL1 inhibitor, a LAG-3 inhibitor, a TEVI-3 inhibitor, a TIGIT inhibitor, and combinations and/or derivatives thereof.

In another example of the third aspect, the inhibitor of an immunoregulatory protein is a TGF-beta inhibitor.

In another example of the third aspect, the TGF-beta inhibitor is selected from the group consisting of galunisertib, EW7203, EW7197, belagepumatucel-L, fresolimumab, gemogenovatucel-T, trabedersen, XOMA089, and a genetic modification of the cells with a dominant negative TGF-beta RII.

In another example of the third aspect, wherein the expanded cells are administered concomitantly with a cytokine support and a TGF-beta inhibitor.

In yet another example of the third aspect, the expanded cells are administered in a dose of at least $10^6$ cells/kg.

In another example of the third aspect, the expanded cells are administered in a dose of at least $10^9$ cells/kg.

In an example of the third aspect, the recipient in need thereof has a cancer.

In certain examples of the third aspect, the cancer is a solid tumor, a blood cancer or a metastatic cancer.

In yet another example of the third aspect, the blood cancer is selected from the group consisting of AML, myeloma, T cell leukemia, Non-Hodgkin's Lymphoma and B cell leukemia, Myelodysplastic syndromes, CLL, and CML.

In another example of the third aspect, the solid tumor is selected from the group consisting of a colon cancer, a prostate cancer, a sarcoma, a pancreatic cancer, and a breast cancer.

In another example of the third aspect, the cancer is a metastatic cancer.

In yet another example of the third aspect, the metastatic cancer is one or more of a lung metastasis or a liver metastasis.

In another example of the third embodiment, the recipient in need thereof has a viral infection. In some aspects, the viral infection is coxsackievirus, human immunodeficiency virus (HIV), hepatitis C virus (HCV), influenza virus, poxvirus, or herpesviruses.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments. Directional terms as used herein—for example, up, down, right, left, front, back, top, bottom—are made only with reference to the figures as drawn and are not intended to imply absolute orientation.

BRIEF DESCRIPTION OF THE DRAWINGS

The above and other features, examples and advantages of aspects or examples of the present disclosure are better understood when the following detailed description is read with reference to the accompanying drawings, in which.

DETAILED DESCRIPTION

Figure 1:
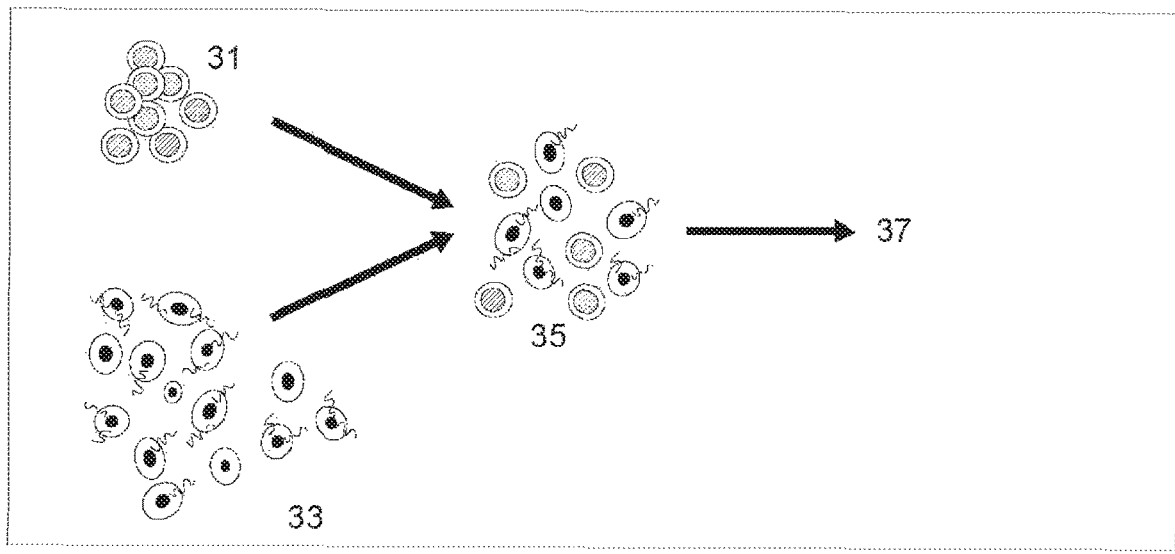
FIG. 1 is a schematic representation of NKF-based NK cell expansion.

Example embodiments will now be described more fully hereinafter with reference to the accompanying figures in which example embodiments and representative data are shown. Whenever possible, the same reference numerals are used throughout the drawings to refer to the same or like parts. However, the embodiments may take on many different forms and should not be construed as limited to those specifically set forth herein. These example embodiments are provided so that this disclosure will be both thorough and complete, and will fully convey the scope of the claims to those skilled in the art.

Directional terms as used herein (e.g., up, down, right left, front, back, top, bottom) are made only with reference to the figures as drawn and are not intended to imply absolute orientation.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the endpoints of each of the ranges are significant both in relation to the other endpoint, and independently of the other endpoint.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. Thus, cells that are "free of" or "substantially free of T cell contamination" for example, are cells to which T cells are not actively added or batched into cell culture, but may be present in very small as a contaminant resulting from natural cell progression during expansion. Similarly, other components may be characterized as "free of" or "substantially free of" in the same manner.

Further, as used herein, the term "consisting essentially of" allows for elements not explicitly recited, but excludes element that affect basic or novel characteristics of the inventions.

Natural killer (NK) cells are potent effectors of the innate immune system with cytotoxic and immunoregulatory function. Human NK cells are typically characterized as lymphocytes expressing CD56 or CD16 and lacking CD3 expression, and are estimated to comprise up to about one-third of peripheral blood lymphocytes in normal subjects. Unlike T-cells, NK cells recognize targets in a major histocompatibility complex (MHC)-unrestricted manner. NK cells play an important role in initiating responses to infection, engraftment, graft-versus-host disease, anti-leukemic activity and post-transplant infection, some of which are reviewed in Lowdell, M. W. Natural killer cells in haematopoietic stem cell transplantation. Transfusion Medicine 2003; 13:399-404.

Regarding cancer specifically, because cancer cells often have reduced or no class I MHC expression, they can become targets of NK cells, and thus, adoptive immunotherapy with NK cells has emerged as a promising anti-cancer treatment. NK cells have therapeutic potential for a wide variety of human malignancies, including sarcomas, myeloma, carcinomas, lymphomas, and leukemias. Until recently, the clinical efficacy and effective application of NK cell immunotherapy has been limited by the inability to obtain sufficient cell numbers for adoptive transfer, as these cells represent a small fraction of peripheral white blood cells, expand poorly ex vivo, and have limited life spans in vivo. The ability to harvest large numbers of peripheral blood lymphocytes through leukapheresis, deplete alloreactive T cells, and activate the remaining NK cells with IL-2 has enabled NK cell adoptive immunotherapy, but this process is expensive, invasive, and remains limited in cell dose to a single infusion of typically less than $2 \times 10^7$ NK cells/kg.

There are various known methods for isolating NK cells from peripheral blood. Generally, to isolate natural killer cells from peripheral blood, PBMCs are separated into lymphocytes and monocytes, and the lymphocytes are further divided into T cells, B cells, and natural killer cells for isolation.

In the present disclosure, the "peripheral blood mononuclear cells," "PBMCs" or "mononuclear cells" refer to mononuclear cells separated from peripheral blood typically used for anti-cancer immunotherapy. The peripheral blood mononuclear cells can be obtained from human blood collected using known methods such as the Ficoll-Hypaque density gradient method. PMBCs may be obtained from a healthy person, a patient at risk of cancer, or a cancer patient. The PBMCs used herein can be, but do not necessarily need to be, autologous; allogeneic PBMCs may also be used to induce and proliferate the NK cells for anti-cancer immunotherapy according to the present disclosure.

In some embodiments, NK cells may be derived from a subject and grown in vitro to provide a population of NK cells for use in the present disclosure. In deriving NK cells from a subject, the cells may come from stem cells or they may be collected from a living donor. In a preferred aspect, the NK cells employed herein are collected from a living donor. In certain aspects, the living donor many be a human living donor. In an alternative embodiment, a NK cell known in the art that has previously been isolated and cultured may be used in the present invention. Thus an established NK cell line may be used. Many such NK cells lines are commercially available and known to those in the art.

Once isolated, NK cells must be expanded if larger numbers are desired. As used herein, "expanded" refers to the increase in number of NK cells by any method. Though several expansion platforms have been developed for NK cells, few have the potential to efficiently produce a large magnitude of highly active NK cells. Such prior art exemplary systems include:

1) Cytokine cocktails: These systems employ various combinations of cytokines (e.g. IL-15/IL-21) and typically lead to several dozen fold expansion. (Wagner J, at al. A Two-Phase Expansion Protocol Combining Interleukin (IL)-15 and IL-21 Improves Natural Killer Cell Proliferation and Cytotoxicity against Rhabdomyosarcoma. Frontiers in immunology. 2017; 8:676.)

2) EBV-LCL feeder line: This system involves an EBV infected feeder line and therefore only a single feeder cell stimulation can be added to the NK cells to ensure eradication of the EBV infected cells which significantly limits the expansion potential of the NK cells. (Berg M, et al. Clinical-grade ex vivo-expanded human natural killer cells upregulate activating receptors and death receptor ligands and have enhanced cytolytic activity against tumor cells. Cytotherapy. 2009; 11(3):341-55.)

3) NK-92 cells: This is an NK cell leukemia cell line that has been used clinically and commercialized by at least two companies. However, these cells must be irradiated as they are cancer cells and that prevents their proliferation in vivo. These cells also have a very short persistence in vivo (~48 hr). (Tonn T, et al. Treatment of patients with advanced cancer with the natural killer cell line NK-92. Cytotherapy. 2013; 15(12):1563-70.)

4) K562 mIL-21 feeder line: This feeder line is often considered the gold standard platform and leads to very similar proliferation and NK cell activation as the NKF cell platform disclosed herein. Despite the promise of these feeder cells, legal issues with multiple institutions have prevented their further development and these cells are no longer being commercialized and cannot be used for future clinical studies. (Denman C J, et al. Membrane-bound IL-21 promotes sustained ex vivo proliferation of human natural killer cells. PloS one. 2012; 7(1):e30264.)

5) Cord blood derived NK cells: The major limitation of using cord blood is a very low starting NK cell population, which limits the scale of proliferation and has significantly higher costs (purchase of cord blood units, differentiation growth factors etc.) (Spanholtz J, et al. High log-scale expansion of functional human natural killer cells from umbilical cord blood CD34-positive cells for adoptive cancer immunotherapy. PloS one. 2010; 5(2):e9221.)

One of the advantages of the systems and methods disclosed herein is the ability to efficiently produce a large magnitude of highly active NK cells. In contrast to most of the prior art expansion systems, including those mentioned above, in certain embodiments of the present disclosure the step of expanding the NK cells provides at least a 10,000- fold expansion within four weeks, such as at least 12,000-fold, at least 14,000-fold, least 16,000-fold, least 18,000-fold, least 20,000-fold, least 22,000-fold, least 24,000-fold, least 26,000-fold, least 28,000-fold, at least 30,000-fold, or at least 32,000-fold expansion within four weeks. In other words, a 4 to 5 week NK cell expansion starting with a peripheral blood pheresis sample from a normal donor (approximately 350×10$^6$ NK cells) will yield approximately 10$^{13}$ NK cells. Since high dose NK cell infusions are typically around 10$^9$/kg, this could yield up to 100 doses per single expansion.

In some aspects of the present disclosure, the administration of the NK cell may be non-immunogenic, for example, by providing a conditioning regimen (e.g. cyclophosphamide and fludarabine) to the patient at the time of administration. The term "non-immunogenic" is thus used broadly herein to mean that when the cell is injected into or otherwise administered to a subject, it avoids detection by the body's immunological system and is not rejected or recognized as foreign. More particularly, the cell does not raise (or is not capable of raising) an immune response sufficient to lead to rejection of the cell and/or to affect the function of the cells. Thus, the cells retain cytotoxic activity in the subject, more particularly, significant or substantial or measurable cytotoxic activity against a target cell. As with any biological system, the absence of an immune response may not be absolute (or 100%), A small (or mild or minor) immune response to the NK cell (e.g. a de minimis immune response) may be tolerated, as long as the function or utility of the cells is not substantially affected (i.e. as long as the cells can still perform their function). That is, the NK cells employed herein may be "universal" in nature such that one set of donor cells can be used for virtually any patient without generating a negative immune response.

Such a universal donor approach will allow for "off-the-shelf" NK cells that will dramatically reduce the cost and increase the accessibility of the disclosed therapeutic strategy worldwide. The ability to harvest allogeneic NK cells from one donor and expand those cells to obtain the doses needed for dozens of unrelated patients would address the major limits of this therapeutic approach. NK cells, unlike T-cells, does not cause GVHD, and therefore, it is thought that they can be safely administered without regard to HLA matching. Besides cost and feasibility, another benefit of the universal donor approach is the potential for identifying donors that are predicted to have the most cytotoxic NK cells. Stem cell transplant donors with a genotype that encodes a preponderance of activating KIRs (B-haplotypes) have been shown to result in improved clinical outcomes (disease free survival, overall survival and GVHD) following allogeneic stem cell transplantation for myeloid leukemia. Finally, utilizing a donor not matched by HLA to recipients also increases the potential for NK cell alloreactivity to promote a "graft vs. leukemia" effect, which has been found to improve disease free survival in certain cancer populations.

In this regard, the NK cells of the present invention may be autologous or allogeneic NK cell. "Autologous" NK cells are cells derived from the patient. "Allogeneic" NK cells are derived from another individual, having non-identical gene at one or more loci. If the NK cells are derived from an identical twin, they may be termed "syngeneic". In particularly preferred embodiments, the NK cells employed according to the disclosed methods, including the methods of treating cancer, are allogeneic NK cells.

To address the limitations on widespread use of NK cell adoptive transfer therapy, the disclosure herein provides a composition of feeder cells methods employing such which allow for the robust expansion of an NK cell system. As used herein, the term "feeder cells" refers to cells that, due to their metabolic activity, produce various metabolites to thereby assist in the proliferation of target cells, even though these cells cannot themselves proliferate.

Feeder cells as used according to the present disclosure may be any population of leukemia cells engineered to express a membrane-bound interleukin (mbIL). As used herein, the term "interleukin (IL) protein" refers to a collection of biologically active cytokines produced by immune cells such as lymphocytes, monocytes or macrophages. According to the present disclosure, the term "cytokine" refers to an immune activating cytokine (secreted protein and/or signaling molecule) that can be used to induce NK cells isolated from PBMCs. Examples of IL proteins which may be used in the present disclosure include IL-2, IL-7, IL-12, IL-15, IL-18, IL-21, Flt3-L, SCF, IL-7 and the like.

In certain aspects of the disclosure, the feeder cells are HL-60 cells or OCI-AML3 cells. In a preferred aspect, the feeder cells are OCI-AML3 cells. Preferably, the mbIL comprises one or more of IL-15 or IL-21. In a preferred aspect, the mbIL consists of, or consists essentially of, mbIL-15. In another preferred aspect, the mbIL consists of, or consists essentially of, mbIL-21.

The cells that are used as feeder cells according to the present disclosure may be non-inactivated or inactivated cells whose proliferation was inhibited prior to use. More specifically, the feeder may be inactivated to ensure their safety and to eliminate their potential to proliferate when employed as part of the feeding platform described herein. A common method for inactivating feeder cells comprises the step of irradiating the killer cells with gamma-rays. If non-inactivated feeder cells are used, they can be killed by natural killer cells during culture because they are tumor cells. In a preferred aspect of the present disclosure, the feeder cells are inactivated using gamma radiation prior to adding them to the cell culture comprising NK cells. In some embodiments, the feeder cells can be inactivated using 10 Gy or greater or of radiation, such as 10 Gy, 20 Gy, 30 Gy, 40 Gy, 50 Gy, 60 Gy, 70 Gy, 80 Gy, 90 Gy, 100 Gy, 110 Gy, 120, Gy, 130 Gy, 140 Gy, 150 Gy, 175 Gy, 200 Gy, 225 Gy, 250 Gy, 300 Gy, 350 Gy, 400 Gy, 450, Gy or 500 Gy. In preferred methods, the feeder cells are inactivated using 90 Gy of gamma radiation.

As used herein, the term "cytotoxic" refers to a cell capable of inducing cell death by lysis or apoptosis in a target cell.

The term "target cell" refers to any cell which is killed by the cytotoxic cells of the invention. More particularly, the target cell is the cell targeted by the NK cells. Thus the target cell may be any cell in the body of the subject which it is desired to abrogate, e.g. to remove, kill, render inactive etc. Preferred target cells are virally infected cells and cancer cells, but target cells may be any cells resulting from a disease or clinical condition that may benefit from adoptive cell transfer therapy. As well as cancer cells, other cells that it may be clinically desirable to remove include infected cells, that is cells infected with any pathogen such as virus-infected cells, or cells infected with any other pathogenic organism, e.g. any microorganism, for example, bacteria, fungi, *mycoplasma*, protozoa, or prions.

Due to their high cytotoxicity against cancer cells, the adoptive transfer of NK cells into cancer patients is a promising therapeutic strategy. As used herein, the term "adoptive transfer" means the transfer of cells into a patient. Support for NK cells use in cancer therapy can be seen from the correlation of the presence and activity of tumor-infiltrating NK cells in a variety of cancers. Several types of cancers, including hematologic malignancies, sarcoma, neuroblastoma, and ovarian cancer have been found to be particularly sensitive to NK cell therapy, and in some cases, improved outcomes have been observed. However, three key obstacles have impeded the widespread clinical use of NK cells as set forth above, including: 1) lack of a robust ex vivo NK cells expansion system; 2) insufficient NK cell activity; and 3) maintenance of activity and proliferation of NK cells in cancer patients despite a highly immunosuppressive tumor microenvironment.

To address the limitations of lack of a robust expansion platform and insufficient NK cell activity, the present disclosure reports a novel ex vivo expansion platform (termed "NKF") that leads to vastly improved numbers of highly active NK cells. The NKF platform described herein employs a feeder cell line constructed from an AML cells line transduced with a membrane-bound IL protein. In some aspects of the present disclosure, OCI-AML3 cells, HL-60 cells, or combinations thereof, are employed as the feeder cell line. Preferably, OCI-AML3 cells are employed as the feeder cell line.

Without wishing to be bound by theory, the presence of membrane-bound IL proteins such as membrane-bound IL-15 (mbIL-15) or membrane-bound IL-21 (mbIL-21) is believed to prevent NK cells from undergoing senescence, markedly improving their ability to expand ex vivo. There are a myriad of studies proposing how and why cytokines exert their effect on NK cell function and prevention of senescence, but a single, clear explanation has not yet emerged. The feeder cells of the present disclosure preferably comprise mbIL-15, mb-IL-21 or combinations thereof as the membrane-bound IL protein.

The polypeptide sequence of mbIL-21 as employed in the present disclosure is identified in SEQ ID NO:1. In certain aspects of the present disclosure, the feeder cell line has been engineered to express a polypeptide of SEQ ID NO: 1, or a sequence having at least 80% sequence identity (or sequence homology) to the amino acid sequence of SEQ ID NO: 1, such as 80%, 85%, 90%, 95%, 99% or 100% sequence homology to SEQ ID NO:1. Alternatively, the feeder cells can be modified by introducing a polynucleotide that encodes a polypeptide having at least 80% sequence identity to the amino acid sequence of SEQ ID NO:1. Once such polynucleotide includes SEQ ID NO:2.

The polypeptide sequence of mbIL-15 as employed in the present disclosure is identified in SEQ ID NO:3. In certain aspects of the present disclosure, the feeder cell line has been engineered to express a polypeptide of SEQ ID NO:3, or a sequence having at least 80% sequence identity to the amino acid sequence of SEQ ID NO:3, such as 80%, 85%, 90%, 95%, 99% or 100% sequence homology to SEQ ID NO:3. Alternatively, the feeder cells can be modified by introducing a polynucleotide that encodes a polypeptide having at least 80% sequence identity to the amino acid sequence of SEQ ID NO:3. Once such polynucleotide includes SEQ ID NO:4.

In certain aspects of the present disclosure, the feeder cells have been engineered to express both mbIL-15 and mbIL-21. In other words, the feeder cells have been engineered to express both a polypeptide of SEQ ID NO: 1, or a sequence having at least 80% sequence identity to the amino acid sequence of SEQ ID NO:1 and a polypeptide of SEQ ID NO:3, or a sequence having at least 80% sequence identity to the amino acid sequence of SEQ ID NO:3.

The feeder cells according to the present disclosure can be further modified to express one or more associated accessory signaling polypeptides, cytokines or fragments thereof. Such expression may correlate with increased expression of the mbIL proteins in certain aspects.

"Sequence homology" or "sequence identity" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

Also included in the present disclosure are methods for expanding NK cells ex vivo. Referring to FIG. 1, the method comprises the steps of harvesting donor cells from a subject; isolating the NK cells 31; and expanding the NK cells in the presence of NKF (feeder) cells 33. In certain aspects, the NK cells can be co-cultured with a cytokine support 35. In other aspects of the disclosed methods, the NKF cells can be refreshed 37.

More specifically, donor cells can be harvested from a subject according to known methods, such as those detailed above. As noted above, donor cells can be cells donated from a living donor or cells harvested from cord blood. The cells can be from a human. In a preferred aspect, the cells can be harvested from a universal living human donor. Once collected, the NK cells can be isolated from PBMCs according to known methods, such as those described above, to provide isolated NK cells 31.

The isolated NK cells 31 are then expanded in the presence of NKF feeder cells 33 in a pre-determined ratio. In certain aspects, the NKF cells 33 are OCI-AML3 cells or HL-60 cells. In a preferred aspect, the feeder cell line comprises OCI-AML3 cells that have been engineered to expressed a mbIL protein, such as those detailed above. In a particularly preferred embodiment, the NKF cells are OCI-AML3 cells that have been engineered to express one or more of mbIL-15 or mbIL-21. In some aspects of the present method, the ratio of NKF cells to NK cells is preferably greater than or equal to about 1:1, such as about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1, based on the number of NK cells counted on the day of the NKF cell addition. In some aspects, a 5:1 ratio of NKF:NK cells is particularly preferred. In other aspects of the present method, the NKF:NK cell ratio is about 10:1, or greater, such as 10:1, 15:1, 20:1, 25:1 or 30:1, based on the NK cell count on the day of the NKF cell addition. In a particularly preferred embodiment, the NKF:NK cell ratio is 10:1.

In addition to the NKF cells, NK cells can be expanded in vivo or ex vivo in the presence of cytokine support 35. Cytokine support 35 is used to enable the cells to survive and proliferate after infusion into the patient. Exemplary cytokines for use according to the disclosed methods include IL-2, IL-15, ALT-803, hetIL-15, IL-12, IL-18, IL-21 or fragments or derivatives thereof. The present methods may comprise the use of more than one cytokine support. In preferred aspects of the present methods, NK cells may be expanded in the presence of IL-2, IL-15 or ALT-803 or other IL-15 derivatives. Alternatively, cytokine support can be provided by engineering the NK cells to express additional cytokines. For example, this can be accomplished by transducing genes for one or more of mbIL-15, soluble IL-15, soluble IL-21, mbIL-21, mbIL-2, or soluble IL-2 into the NK cells prior to or after NK cell expansion. In some aspects of the disclosure, cytokine support is provided by pharmacologic inhibitors. In some aspects of the disclosure, cytokine support is provided by genetic modification. In other aspects, cytokine support can be provided both pharmacologically and genetically.

A novel IL-15 superantagonist called ALT-803 has recently been developed that offers the potential to markedly improve the survival/proliferation of adoptively infused NK cells. (Zhu, X. et al. Novel Human Interleukin-15 Agonists. J. Immunol. 2009; 183(6):3598-3607, herein incorporated by reference). ALT-803 is a fusion protein containing a mutated IL-15 molecule fused to a portion of the IL-15 receptor (αSu/Fc fusion protein). ALT-803 exhibits greater than 25-fold enhancement in biological activity compared to IL-15 and a markedly improved half-life (25 hrs).

In certain aspects of the disclosed methods, the expanding of NK cells in the presence of NKF cells can last up from one to eight weeks. That is, the step of expanding NK cells can take, e.g., one week, two weeks, three weeks, four weeks, five weeks, six weeks, seven weeks, or eight weeks.

When NK cells are expanded for more than one week, the NKF cells may need refreshed or replenished throughout the step of expanding the NK cells. Refreshing of NKF cells can be done on an as-needed basis, preferably weekly. The amount of NKF cells for refreshment can employ the same ratio of NKF:NK cells as the starting ratio or the NKF cells can be replenished in a different ratio as needed. In some aspects of the present method, the ratio of NKF cells to NK cells of refreshment is preferably greater than or equal to about 1:1, such as about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1, based on the number of NK cells counted on the day of the NKF cell addition. In some aspects, a 5:1 ratio of NKF:NK cells is particularly preferred. In other aspects of the present method, the NKF:NK cell ratio is about 10:1, or greater, such as 10:1, 15:1, 20:1, 25:1 or 30:1, based on the NK cell count on the day of the NKF cell addition. In a particularly preferred embodiment, the NKF:NK cell ratio is 10:1.

As demonstrated below, the expansion potential of the disclosed methodology is vastly improved compared to prior art systems. In certain aspects of the claimed methods, the step of expanding the NK cells provides at least a 10,000-fold expansion of NK cells within 4 weeks. That is, after four weeks of culturing NK cells in the presence of NKF cells (replenished weekly), there are at least 10,000 more NK cells present than were present in the starting culture. In some embodiments, the step of expanding the NK cells provides at least a 20,000-fold expansion of NK cells within 4 weeks. In other embodiments of the disclosed methods, the step of expanding the NK cells provides at least a 30,000-fold expansion of NK cells within 4 weeks.

Once large numbers of NK cells can be obtained, NK cells can be used as cytotoxic agents against cancer cells. In some aspects are methods of treating cancer in a recipient subject in need thereof, said method comprising: (a) harvesting donor cells from a donor subject; (b) isolating the NK cells from the donor cells; (c) expanding the NK cells according to any of the methods detailed herein; (d) administering the expanded NK cells to the recipient subject.

As demonstrated below, NK cells expanded according to the disclosed methods demonstrated markedly increased cytotoxic activity against a wide variety of cancer cells lines, both in vitro and in vivo.

NK cell therapy has shown clinical promise against a wide variety of tumor types, including both solid tumors and blood cancers. The therapeutic approaches described herein can be used as treatment of virtually all types of cancers and pre-cancers (e.g. Myelodysplastic syndrome), including but not limited to carcinomas, sarcomas, melanomas, lymphomas, and leukemias, and having places of origin including but not limited to colon, prostate, brain, breast, liver, lung, pancreatic, bone, ovarian, skin, pancreatic, blood and others. The methods disclosed herein are contemplated for treatment of both metastatic cancers as well as primary tumor sites.

NK cell therapy has also been employed to treat viral infections, including coxsackievirus, human immunodeficiency virus (HIV), hepatitis C virus (HCV), influenza virus, poxvirus, and herpesviruses, with highly positive clinical outcomes. Without wishing to be bound by theory, it is believed that NK cells control viral infections, in part, by secreting IFNγ and TNFα. The methods disclosed herein are contemplated for treatment of viral infections. In a preferred embodiment, the methods disclosed herein can be used to treat HIV infections.

In certain aspects of the claimed methods, NK cells expanded according to the disclosed methodologies can be administered in dosages amounts ranging from $10\text{-}10^{12}$ cells/kg. Preferred dosage amounts range from $10 \times 10^6$ cells/kg to $10,000 \times 10^6$ cells/kg and are preferably in the range of $1,000 \times 10^6$ cells/kg. Dosage amounts can be adjusted on a per patient or a per administration basis as needed throughout the treatment cycle.

NK cells expanded according to the disclosed methodologies can be administered to patients via infusion. Preferably, cell transfers occur biweekly, once weekly, once every two weeks, once every three weeks, once every four weeks, once every five weeks, once every six weeks, or on an as-needed basis. In a preferred embodiment, NK cells infusions will be administered in two week intervals.

For administration to patients, NK cells expanded according the disclosed methodologies can be administered in combination with (concomitantly or sequentially) a standard conditioning regimen. Such regimens are well established in the art and can include, e.g. cyclophosphamide and fludarabine. Without wishing to be bound by theory, conditioning regimens are thought to deplete host T cells and enable chimeric antigen receptor T (CAR-T) cells to expand, as well as enable the infused cells to utilize host cytokines, such as IL-15 and IL-7, fully. Such regimens are necessary for the survival of adoptively infused allogeneic NK cells, and are used even for autologous cell transfers.

When NK cells expanded according to the disclosed methods are administered in combination with cytokine support, exemplary cytokines for administration include IL-2, IL-15, ALT-803, hetIL-15, IL-12, IL-18, IL-21 or active fragments or derivatives thereof. Cytokine support is typically administered via s.c. or i.v. injection at doses ranging from 0.1 to 1000 µg/kg, preferably at doses of 10 µg/kg. Cytokine support can be co-administered, administered sequentially or administered concomitantly. In some aspects of the present disclosure, cytokine support can be administered up to two weeks, one week, or one day prior to NK cell infusion, or on the day of infusion. In some aspects of the present disclosure, administration of cytokine support can continue beyond the administration of NK cells. In a preferred aspect of the present disclosure, cytokine support will be administered weekly throughout the NK infusion cycle.

In addition to the need to obtain large quantities of highly active NK cells ex vivo, long term clinical development also requires strategies to maintain their activity in vivo. It has been shown that TGFβ significantly impairs NK function, thus, markedly impairs the in vivo activity of adoptively transferred NK cells (See e.g. Otegbeye, E. et al. Inhibiting TGF-beta signaling preserves the function of highly activated, in vitro expanded natural killer cells in AML and colon cancer models. PLOS One, 2018; 12(1):e019138. E pub 2018/01/18. Doi: 10.1371/journal.pone.0191358. Pub Med PMID: 29342200; PMCTD: PMC5771627.) There is also an established relationship between GSK3 activity and NK function. More specifically, GSK3-inhibited NK cells show significant efficacy in AML mouse models compared to non-GSK3-inhibited NK cells. (See e.g. Parameswaran P. et al. Suppression of GSK3 restores NK cell cytotoxicity in AML patients. Nature Communications. 2016; 7:1 1154. Doi 10.1038/ncommsl 1154. PubMed MPID: 27040177; PMCID: PMC4822012.) Thus, in some aspects of the disclosed methods, NK cells expanded according to the disclosed methods comprise co-administration, concomitant administration or sequential administration of NK cells and TGFβ and/or GSK3 inhibitors. In a preferred aspect of the present disclosure, treatment comprises co-administration of a TGFβ inhibitor, e.g. galunisertib, EW7203, EW7197, belagepumatucel-L, fresolimumab, gemogenovatucel-T, trabedersen, XOMA089. In a preferred aspect, the TGFß inhibitor is galunisertib. TGF-beta and/or GSK3 inhibitors can be administered in doses ranging from 0.1 to 1000 µg/kg, and can be administered daily, weekly, monthly or dose frequency can be adjusted based on the needs of the patient.

Alternatively, TGF-beta signaling can be inhibited genetically, that is, by the genetic modification of the NK cells to express one or more proteins that impair TGF-beta signaling. This strategy has been successfully employed, for example, utilizing a dominant negative TGF-beta receptor II (TGF-beta RII), a gene encoding a truncated form of the transmembrane protein transforming growth factor, beta receptor II. (Chen, R.H. et al. Inactivation of the type II receptor reveals two receptor pathways for the diverse TGF-beta activities. Science 1993;260 (5112): 1335-1338. Kloss, C. et al TGFBeta Signaling Blockade within PSMA Targeted CAR Human T Cells for the Eradication of Metastatic Prostate Cancer. Molecular Therapy 2016; 24(S1): S252-253.) In certain aspects of the disclosed methods, TGFβ signaling is impaired through the overexpression of the dominant negative TGF-beta RII, or by disrupting other TGFβ signaling molecules.

EXAMPLES

Development and Optimization of IL-21-Based Feeder Expansion Platform

The basis for the methodology employed herein is a genetically manipulated feeder cell line (so-called "NKF" cells) that comprises a leukemia cell line in which mbIL-21 has been expressed. In developing the NK cell expansion platform, the feeder cell line was selected to comprise cells that are efficiently lysed by NK cells and further exhibit a low level of expression of HLA class I molecules. A low level of HLA class I proteins is believed to be beneficial as certain epitopes are recognized by NK cell inhibitory killer inhibitory receptors (KIRs), which impair NK cell activation in vivo.

According to the disclosed methods, NKF cells are irradiated to prevent their expansion and then co-cultured with NK cells. NKF cells are rapidly killed by NK cells during the co-culture, leading to concomitant expansion of the NK cells. Unlike traditional NK cell expansion methods that are limited by rapid NK cell senescence and thus, limited proliferation, NK cells expanded by the disclosed process proliferated for extended durations (at least two months) and lead to robust proliferation (up to 30,000-fold within 4 to 5 weeks). Without wishing to be bound by theory, the prevention of senescence is believed to be due partially to the mbIL-21 on the feeder cells.

The novel NK cell expansion platform according to the present disclosure has been developed employing either OCI-AML3 or HL-60 cells, both of which are myeloid leukemia cells lines with the ability to expand rapidly, maintain good viability at high densities, and have low levels of HLA class I expression.

Example 1—Development of NKF Cell Platform

To assess their expansion potential, OCI-AML3 (this line is commercially available from, e.g. DSMZ, Braunschweig, Germany, it is not available at ATCC) and HL-60 cells (also commercially available from, e.g., DSMZ, Braunschweig, Germany) cells were cultured in RPMI 1640 media (Hyclone) supplemented with 10% calf serum (Hyclone), penicillin (100 U/mL), and streptomycin (100 µg/mL). Testing for *Mycoplasma* contamination was performed on all cell lines at regular intervals using the *Mycoplasma* Detection Kit-Quick Test (www.bimake.com). Once cultured and collected, the OCI-AML3 or HL-60 cells were irradiated using gamma irradiation (30 Gy) to obtain irradiated feeder cells.

Figure 2:
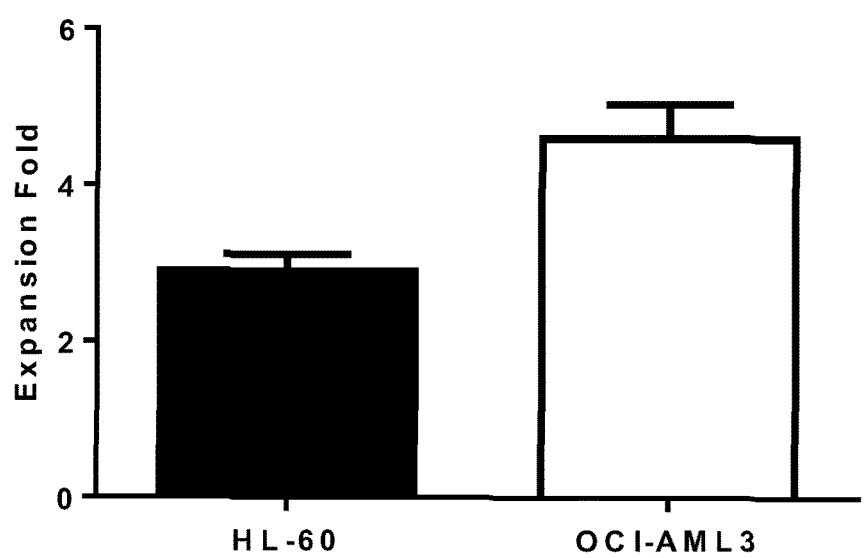
FIG. 2 is a graph demonstrating fold expansion of NK cells after 1 week incubation using HL-60 (left) and OCI-AML3 (right) cells as feeder cells provided at 5:1 ratios.

Peripheral blood mononuclear cells (PBMC's) were isolated from peripheral blood of healthy human donors via FICOLL (GE Healthcare) gradient centrifugation. NK cells were isolated from PBMC's through magnetic bead CD3 depletion and in some cases, further purification was performed by CD56 isolation (Miltenyi Biotec). NK cells were cultured in RPMI 1640 media (Hyclone) supplemented with 10% calf serum (Hyclone), penicillin (100 U/mL), and streptomycin (100 µg/mL). To the culture media were added irradiated feeder cells (5:1 or 10:1 feeder cell:NK cell ratio, based on NK cell count on the day of addition) as well as IL-2 (range of 10-1000 units/mL) and the cells were incubated for 1 week at 37° C. in a tissue culture incubator with 5% $CO_2$. Referring to FIG. 2, the OCI-AML3 cell line (unfilled bar) led to a 4.6-fold expansion over a 1-week incubation period as measured by cell counting using a hematocytomer. The HL-60 cells (solid bar) led to a 2.9-fold expansion over this time period. Thus, OCI-AML3 cells demonstrated improved expansion capability compared to HL-60 cells.

Figure 3:
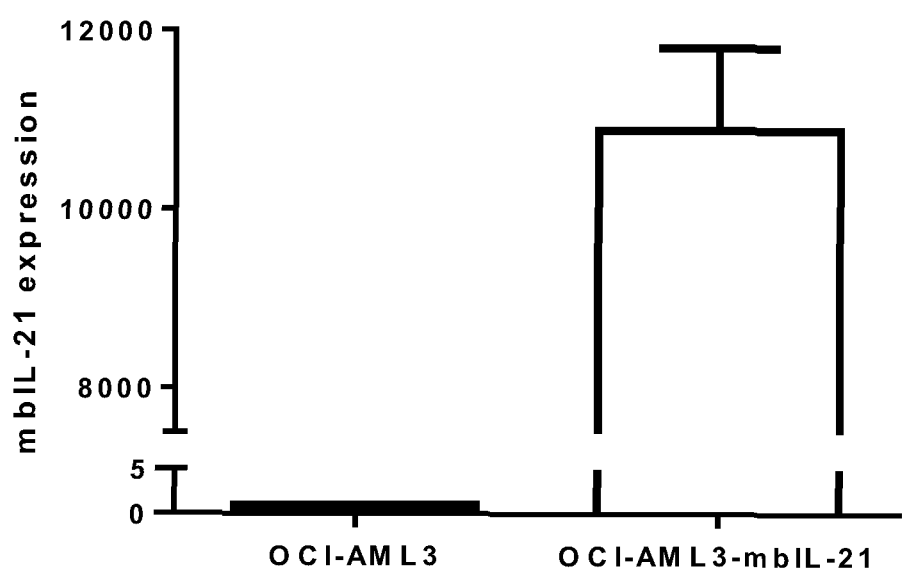
FIG. 3 is a graph demonstrating expression of mbIL-21 as determined by rt-PCR in OCI-AML3 (left) and OCI-AML3-mbIL-21 (right) cells.

In order to improve on this expansion, OCI-AML3 cells were transduced to express membrane-bound IL-21. 293T cells were co-transfected with a lentiviral plasmid encoding mbIL-21 (VectorBuilder, Santa Clara, CA) and packaging plasmids VSVG and R8.74 using Turbofect (Thermo Fisher, Pittsburgh, PA). The polynucleotide sequence for the lentivirus plasmid for mbIL-21 expression is indicated in SEQ ID NO: 5 of the included sequence listing. Alternatively, 293T cells can be co-transfected with a lentiviral plasmid encoding mbIL-15 (SEQ ID NO: 6) or both mbIL-21 and mbIL-15 (SEQ ID NO:7). The studies shown herein employ cells expressing mbIL-21 only. Approximately 1 million OCI-AML3 cells were infected with 100 microliters of virus containing supernatant concentrated ~20 fold overnight in 12.5% PEG in the presence of 6 μg/mL of polybrene. The virus was washed off the following day and stable cells lines were generated by selection with puromycin (1 μg/mL) approximately 72 hours after transduction. FIG. 3 reports an rt-PCR assessment of mbIL-21 expression in OCI-AML3 cells prior to transduction (solid bar) compared to OCI-ALM3 cells following transduction (unfilled bar). After lentivirus transduction, mbIL-21 is expressed at levels approximately 8,000-12,000 greater than native OCI-AML3 cells (data normalized). In some aspects of the present disclosure, the NKF cells comprise OCI-AML3 cells expressing mbIL-21.

As shown schematically in FIG. 1, following transduction with mbIL-21, NK cells isolated according to the procedure detailed above were co-cultured with irradiated NKF cells procured as detailed herein. To the NK-NKF cell co-culture was added IL-2. NKF cells were replenished weekly throughout the incubation period. Fresh IL-2 was added every 2-3 days during the co-culture period.

Figure 4A:
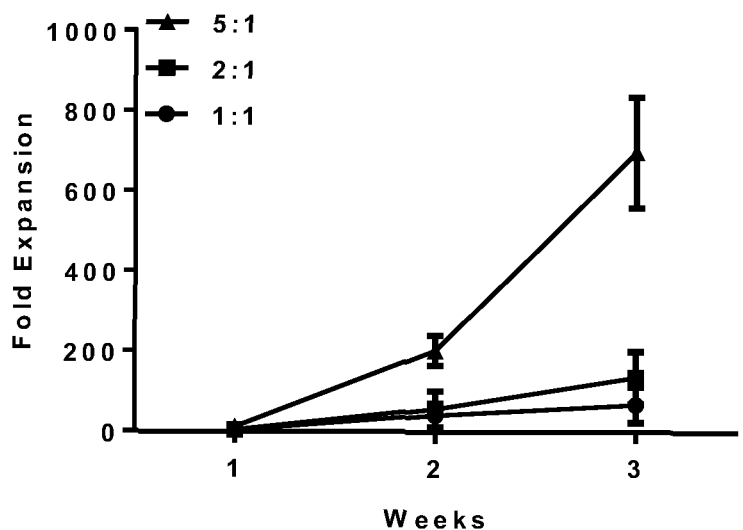
FIG. 4a is a graph demonstrating fold expansion of NK cells expanded with varying NKF:NK cell ratios.
Figure 4B:
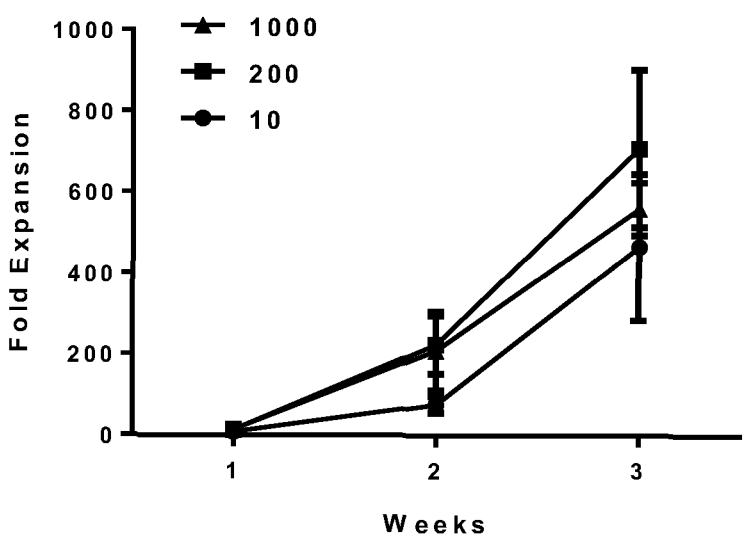
FIG. 4b is a graph demonstrating fold expansion of NK cells expanded with varying concentrations of IL-2.

The herein described NKF expansion platform was optimized based on NKF-to-NK cell ratio in order to generate robust expansion while limiting the feeder cell number to avoid excess dead feeder cells in the final cell product. Using the cell culture procedure detailed above, NK cells were incubated for a period of 3 weeks, with once-weekly additions of NKF cells. The NKF cells were provided in ratios of 5:1, 2:1 and 1:1 NKF cells:NK cells based on a count of NK cells on the day of addition. Referring to FIG. 4a, after 3 weeks of expansion with NKF cells, the expansion platform comprising the step of adding NKF cells to the NK cell culture in a 5:1 ratio NKF:NK cells (based on cell count the day of the addition) resulted in an 8.3-fold higher expanded NK cell yield compared to a 1:1 ratio, and a 2.7-fold higher expanded NK cell yield compared to a 2:1 ratio. Further studies showed that even higher ratios (e.g. 10:1) led to even higher proliferation rates.

The NKF expansion platform was also optimized based on IL-2 concentration. Referring to FIG. 3b, NK cell expansion yields appeared to be independent of IL-2 concentration, with IL-2 concentrations of 10 U/mL (circles), 200 U/mL (squares) and 1000 U/mL (triangles) not resulting in a statistically significant difference in the proliferative capacity of the feeder cell expansion. Thus, in some aspects of the disclosed methods, the concentration of IL-2 employed the expansion platform ranges from about 10 u/mL to about 1000 U/mL, such as about 10 U/mL, about 50 U/mL, about 100 U/mL, about 150 U/mL, about 200 U/mL, about 250 U/mL, about 300 U/mL, about 350 U/mL, about 400 U/mL, about 450 U/mL, about 500 U/mL, about 550 U/mL, about 600 U/mL, about 650 U/mL, about 700 U/mL, about 750 U/mL, about 800 U/mL, about 850 U/mL, about 900 U/mL, about 950 U/mL, or about 1000 U/mL. In a particularly preferred aspect of the disclosed methods, the IL-2 concentration is 200 U/mL FIG. 5 demonstrates the robust proliferation of NKF cells produced according the present methods. NK cells were isolated from three healthy donors and expanded in the presence of irradiated NKF cells obtained as described above. NKF cells were added weekly in a 5:1 ratio (NKF: NK cells, based on NK cell count the day of the addition) for four weeks in media containing 200 U/mL IL-2. Expansion was rapid between weeks three and four, going from an expansion of about 2500-fold at three weeks to over 15,000-fold at the four week mark. At week four, the total NK cell expansion was between 18,000 and 32,000-fold.

Example 2—Purity of NKF-Expanded NK Cells

Figure 6A:
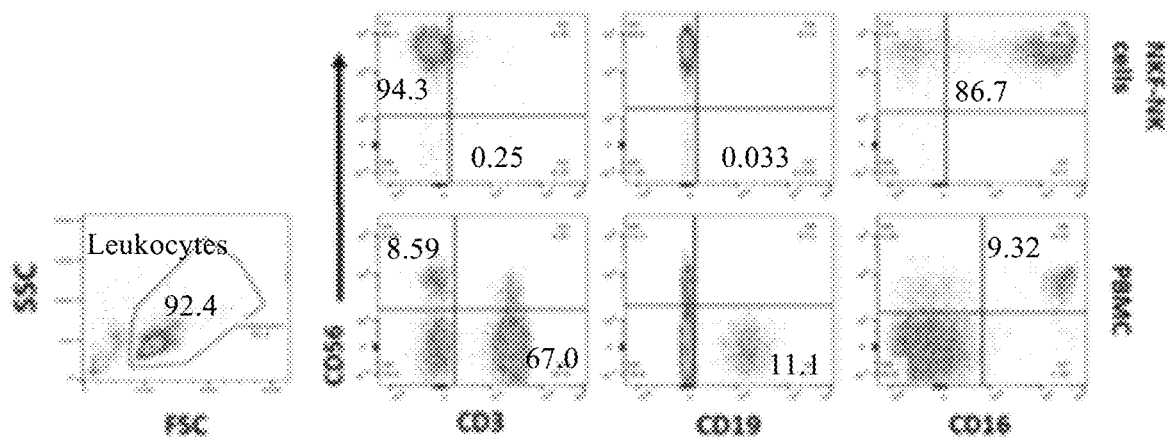
FIG. 6a presents representative flow plots demonstrating purity of NK cells in the initial PBMC cell mixture (bottom row) and after expansion (top row).
Figure 6B:
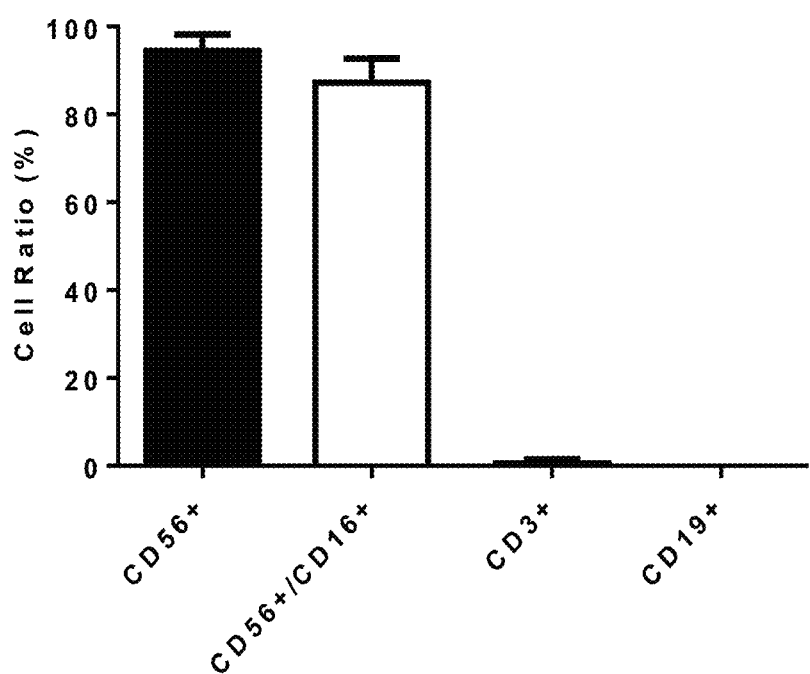
FIG. 6b is a graph demonstrating relative fractions of cell types in NKF-expanded NK cells.

The purity of expanded NK cells was assessed by flow cytometry. FIG. 6a shows representative flow plots depicting the purity of NK cells in the initial PBMC starting population (bottom row) and after expansion with NKF cells (top row). After 2 weeks of expansion employing the methodology detailed herein, CD56+/CD3− cells were approximately 94% of the expanded cells, compared to less than 9% in the PBMC starting population (left column). CD3+ cells made up less than 1% in the expanded NK cells, compared to approximately two-thirds in the starting population (left column, top and bottom panels, respectively). B cells were virtually undetectable in the expanded NK cells which is important to avoid passenger B cells in the NK cell product. Approximately 87% of the expanded NK cells were CD56+/CD16+(FIG. 6a, right column, top panel), suggesting that a large portion of these cells could mediate antibody-dependent cell-mediated toxicity (ADCC). This is in contrast to only about 9% of the NK cells in the pre-processed PBMC fraction were CD56+/CD16+(FIG. 6a, right column, bottom panel). Low T cell contamination post-expansion is important for avoiding potential GVHD after expanded NK cells are utilized as universal donor cells for treating cancer patients, irrespective of HLA matching.

Example 3—Cytotoxic Activity of NKF-Expanded NK Cells

Traditionally, NK cells utilized for adoptive cell therapy are activated by high dose IL-2 prior to administration to patients. It is well established that IL-2 improves cellular cytotoxicity, although the mechanisms for this are not well understood. Without wishing to be bound by theory, it has been hypothesized that the presence of mb IL-21 can prevent NK cells from undergoing senescence, markedly improving their ability to expand ex vivo.

While this IL-2 treatment leads to a relatively high level of NK cell cytotoxic activity, NK cells expanded with the NKF platform disclosed herein unexpectedly exhibited significantly higher activity than NK cells activated with IL-2 according to known methods. NK cell cytotoxic function was assessed by measuring the number of live cells identified by calcein-AM (CAM) labeling. Target cells and NK cells were labeled with CAM (BD Pharmingen, San Jose, Calif.) and calcein-violet (CV) (eBioscience from ThermoFisher), respectively for approximately 15 minutes in the dark at room temperature. NK cells were co-incubated with target cells at the indicated ratios for 4 hours in triplicate at 37° C. in a tissue culture incubator with 5% $CO_2$, and the samples were analyzed by flow cytometry (Attune NXT, Invitrogen) in 96 well plates. The CV-positive NK cells were gated out for analysis. Percent lysis was calculated according to the equation below:

$$\frac{\left(\begin{array}{c}\# CAM \text{ bright} \\ \text{target cells alone}\end{array}\right) - \left(\begin{array}{c}\# CAM \text{ bright cells in } NK \\ \text{and target } co-\text{culture}\end{array}\right)}{\# CAM \text{ bright target cells alone}} \times 100$$

Figure 5:
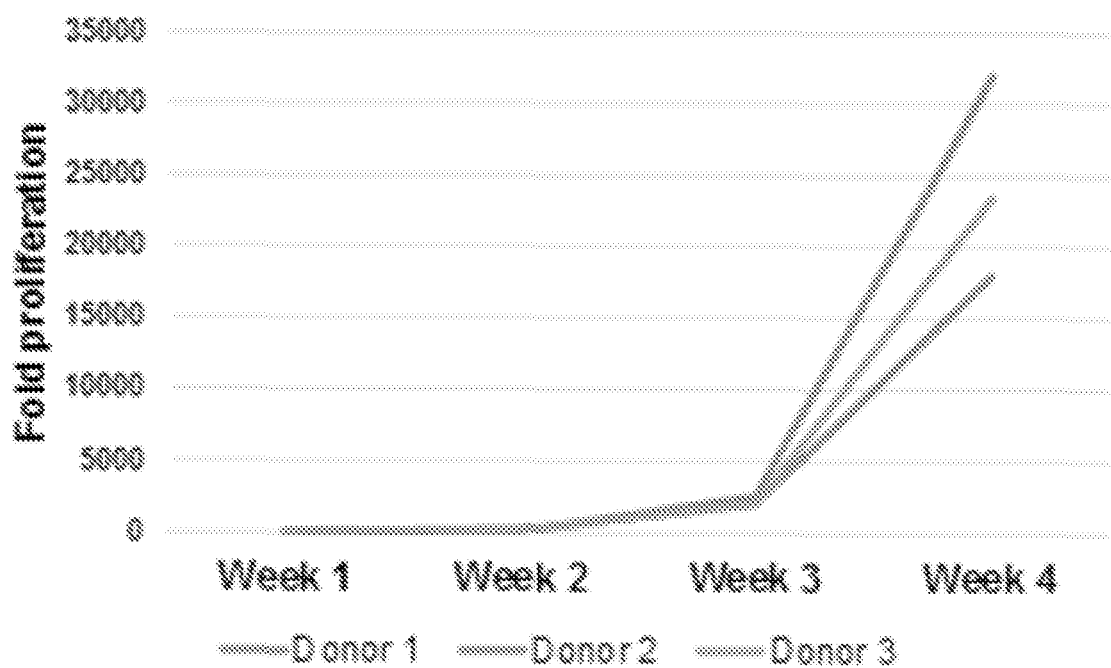
FIG. 5 is a graph demonstrating exemplary proliferation of NK cells expanded according to the disclosed methodology.
Figure 7:
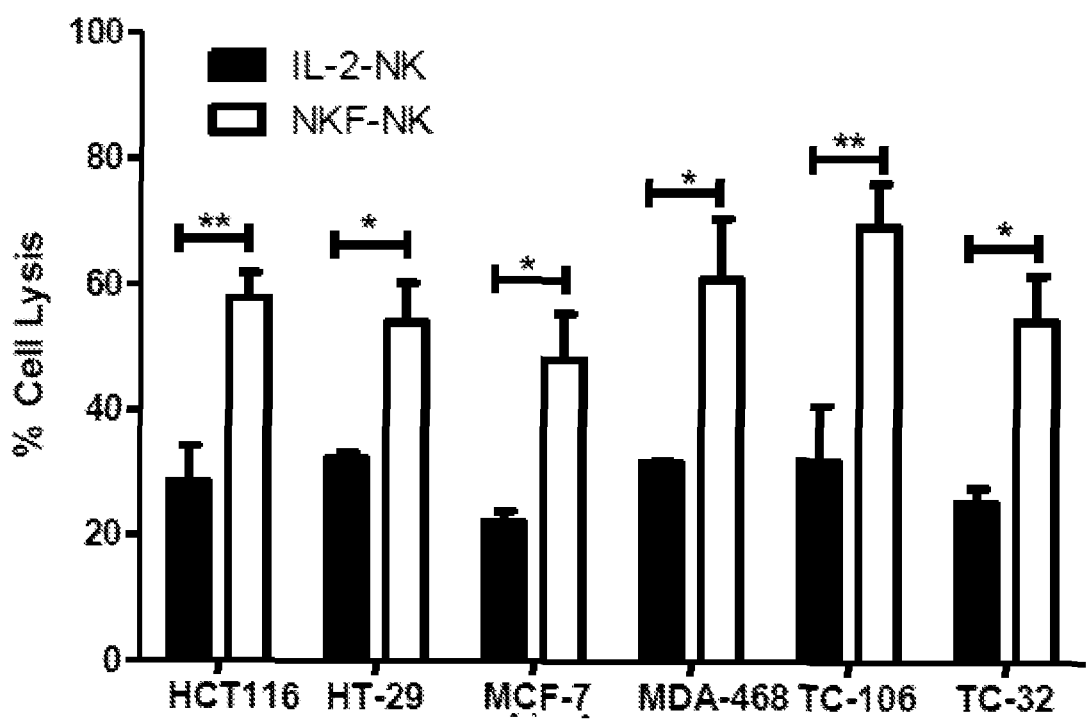
FIG. 7 is a graph demonstrating the high in vitro activity of NKF-expanded NK cells against a variety of cancer cell lines as compared to IL-2 activated non-expanded cells.

FIG. 7 shows the results of cytotoxic activities studies for a variety of cancer cells lines. NK cells expanded with NKF cells or freshly isolated NK cells activated with IL-2 (200 U/mL) overnight were incubated with the indicated cancer cells (from left to right in FIG. 7, x-axis: HCT116, HT-29, MCF-7, MDA-468, TC-106 and TC-32) which had been prelabeled with Calcein AM. The ratio of NK cells:target (cancer) cells was 1:1. After 4 hours, the above-described flow cytometry-based cytotoxicity assay was performed. In all cases, NK cells expanded with NKF cells (open bars) demonstrated significantly greater cytotoxic activity compared to freshly isolated NK cells activated with IL-2 (solid bars). The increase in cell lysis (FIG. 7, y-axis) for the NK cells expanded by the NKF platform (FIG. 5, open bars) varied across the cancer cell lines tested from about a 30% increase to an increase of over 50% compared to non-expanded NK cells activated overnight with IL-2 treatment (FIG. 5, solid bars).

Figure 8:
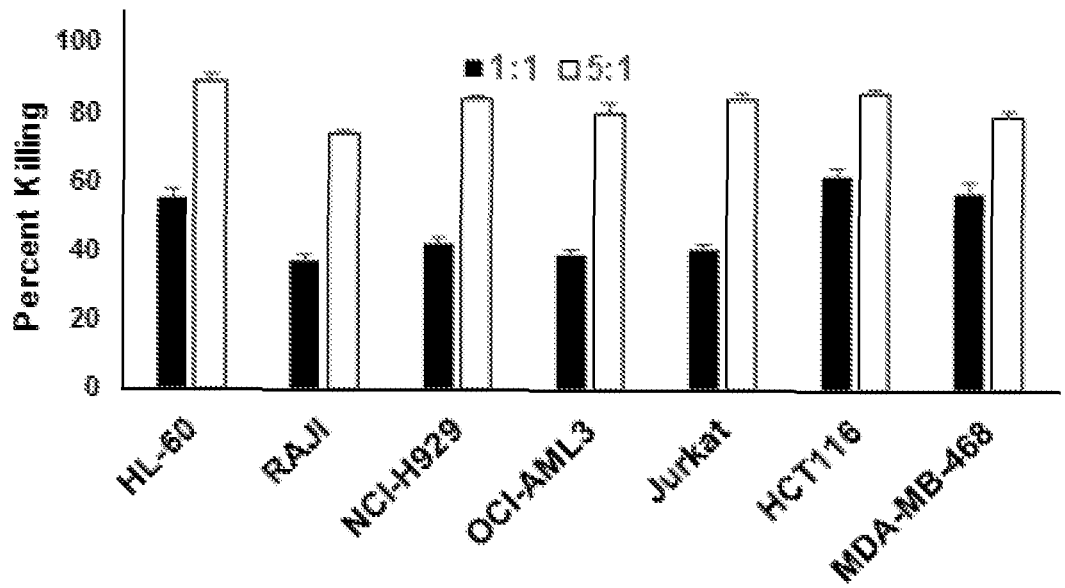
FIG. 8 is a graph demonstrating the high in vitro activity of NKF-expanded NK cells against a variety of cancer cell lines provided at varying NKF:NK cell ratios.

Further, high levels of in vitro cytotoxic activity utilizing the NKF expansion platform were observed across a variety of cancer cell types, including colon, sarcoma, breast cancer and multiple blood cancer cell types. Referring to FIG. 8, NKF-expanded NK cells were tested in a 1:1 (solid bars) and a 5:1 (open bars) NK cell:target cell ratio using the same flow cytometry assay employed for the cell lysis assay described immediately above. As demonstrated in FIG. 8, even at low NK:target cell ratios (1:1), NKF-expanded NF cells demonstrate excellent sensitivity to a variety of cancer cells (e.g., from left to right in FIG. 8: HL-60, RAJI, NCI-H929, OCI-AML3, Jurkat, HCT116, and MDA-MB-468). For example, when employed in a 1:1 NK:target cell ratio, the percent killing (FIG. 8, y-axis) ranged from about 35% to about 65%. When the NK:target ratio was increased to 5:1, the percent killing increased from about 75% to about 90%.

Figure 9:
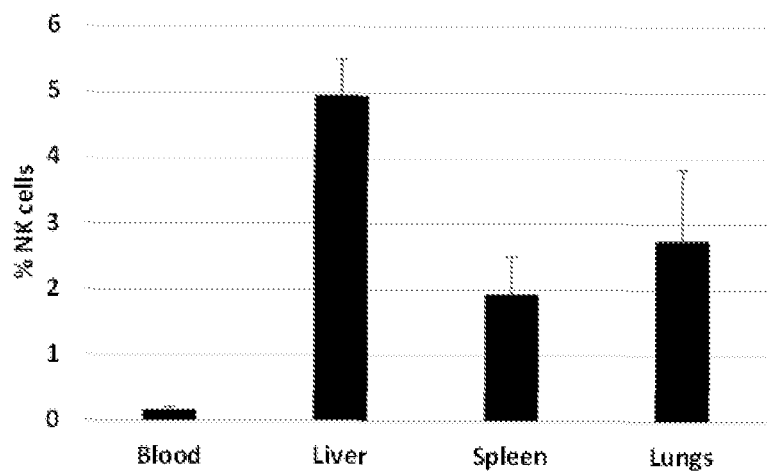
FIG. 9 is a graph demonstrating that NKF-expanded NK cells were efficiently trafficked to the liver and lungs.

Without wishing to be bound by theory, the increased cell killing observed when using the NKF expansion platform reported herein appears to be due to a significant increase in NK cell activating receptors (e.g. NKG2D and NKp30/NKp44), as well as an increase in cell trafficking molecules such as CXCR6 for the in vivo studies. NKp30 and NKp44 are known to play key roles in NK cell killing of colon cancer cells, and CXCR6 is involved in the trafficking of NK cells to the liver, the most common site of colon cancer metastases. In addition to the liver, the NKF-expanded NK cells show a high propensity to traffic to the lungs, making these ideal targets for immunotherapy treatment. Experimentally, NKF-expanded NK cells were labelled with CFSE and injected i.v. into NSG mice. After a 72 hours, single cell suspensions from the indicated organs were prepared and assessed by flow cytometry. As demonstrated in FIG. 9, the organs that were the highest targeted by the NKF-expanded NK cells were the liver (5%) and lungs (3%), followed by the spleen (2%). Very few NK cells were observed in the blood (>0.3%) under these conditions.

Enhancement of Cytotoxic Activity

Not only are large numbers of NK cells necessary for infusion into patients to achieve clinical efficacy, but these cells must also survive and proliferate in vivo for a sustained duration. After infusion of NK cells into patients, cytokine support is used to enable the cells to survive and proliferate. While low dose IL-2 has traditionally been used, it can lead to unwanted proliferation of regulatory T cells and suboptimal NK cell proliferation. IL-15 support has demonstrated better results, however, its use is limited as it requires extremely high doses for meaningful effects and it has an extremely short half-life. As noted above, ALT-803 has shown therapeutic promise in multiple cancer models, but had not been tested in combination with adoptively transferred NK cells.

ALT-803 was tested to assess its potential as cytokine support for adoptive NK therapy in cancer mouse models.

Example 3a—In Vitro Assessment

Figure 10A:
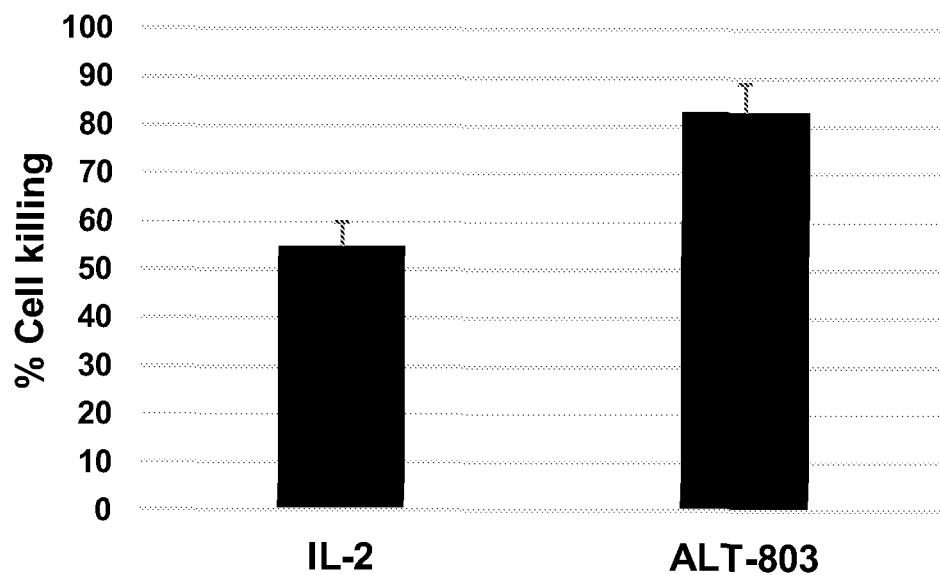
FIG. 10a is a graph demonstrating the enhancement in cell cytotoxicity of ALT-803 compared to IL-2 as cytokine support in vitro.

The activity of NKF-expanded NK cells was tested in combination with IL-2 and ALT-803 according to the cytometry assay described above. NK cells were treated with IL-2 (200 units/mL) or ALT-803 (100 ng/mL) and cytotoxicity against OCI-AML3 cells was measured in vitro using the Calcein AM assay described above. As demonstrated in FIG. 10, both IL2- and ALT-803-supported NK cells resulted in high levels of cytotoxicity. IL-2-supported cells resulted in about 50-60% cytotoxicity (FIG. 10a, left bar). ALT-803-supported cells resulted in about 70-90% killing efficacy (FIG. 10a, right bar). Thus, while both provided functional cytokine support, the activity of NKF-expanded NK+ALT-803 was enhanced by about 33% compared to the activity of NKF-expanded NK+IL-2 in in vitro models.

Example 3b-Mouse Cancer Models

Figure 10B:
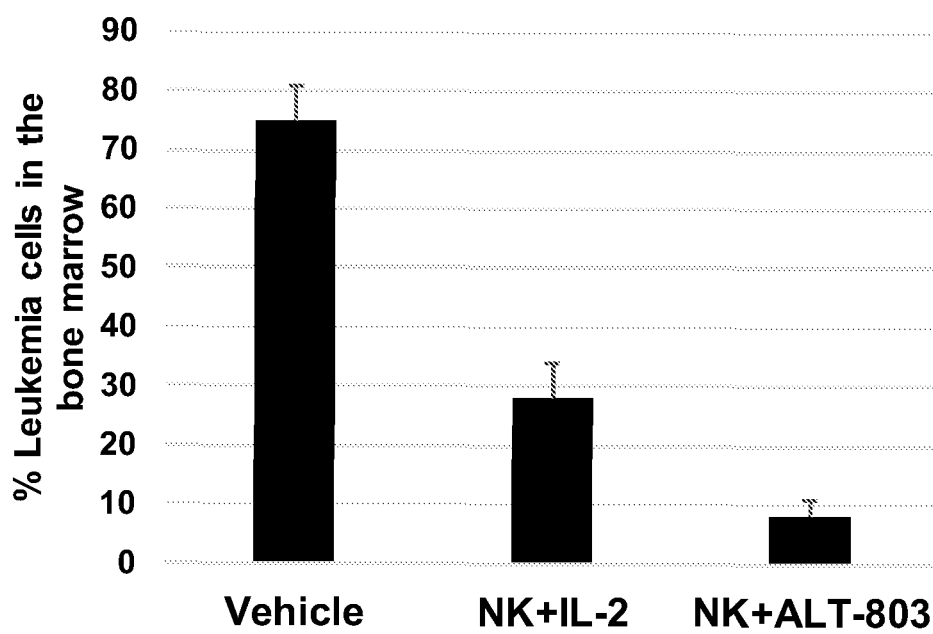
FIG. 10b depicts in vivo cytotoxicity of NKF-expanded NK cells against OCI-AML3 cells in NSG mice.

Employing an AML mouse model, NSG mice (n=5 per group) were injected i.v. with OCI-AML3 cells, and five days later, the mice were injected with $10 \times 10^6$ NKF-expanded NK cells or with vehicle i.v. weekly for 2 weeks. Mice receiving NK cells also received IL-2 or ALT-803 cytokine support. After 4 weeks, the mice were sacrificed and bone marrow was assessed for leukemic burden (FIG. 10b) by flow cytometry as described above. Referring to FIG. 10b, the NK cell treatment led to a significant reduction in leukemia burden for both groups compared to the control vehicle (FIG. 10b, left bar). Mice administered only the control vehicle demonstrated a leukemic burden of about 70-80%. In contrast, mice administered NK cell treatment concomitantly with IL-2 cytokine support demonstrated a leukemic burden of about 25-35% (FIG. 10b, center bar). Mice administered NK cell treatment in combination with ALT-803 cytokine support (FIG. 10b, right bar) had a leukemic burden of about 8-12%. Thus, while treatment with NK cells and cytokine support was significantly improved over vehicle alone, ALT-803 cytokine support was more than twice as effective as IL-2 cytokine support.

Figure 10C:
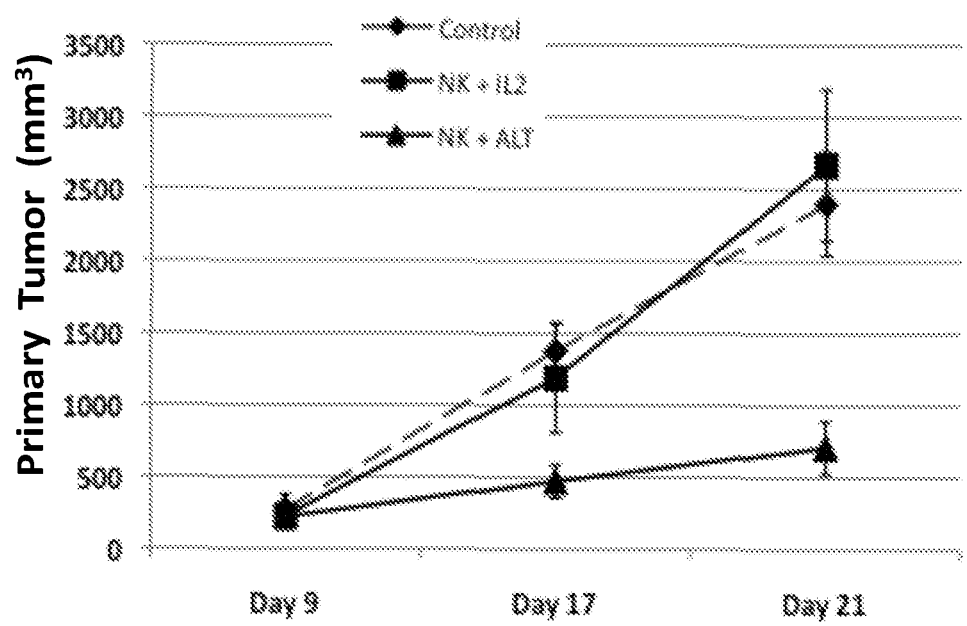
FIG. 10c depicts subcutaneous tumor volume of control and NKF-expanded NK cells in the presence of IL-2 or ALT-803 as cytokine support.

The NKF-expanded NK cells were also tested in a lung metastases model of human sarcoma using TC-106 Ewing's sarcoma cells. In this experiment, $1 \times 10^5$ TC-106 cells were injected subcutaneously into the flanks of NSG mice (n=5 per group). Five million NKF-expanded NK cells were injected i.v. weekly for 2 weeks once tumors reached approximately 100 mm$^3$. The mice were sacrificed after approximately 4 weeks and tumor volume was quantified using standard techniques and the VENTANA imaging software (Ventana Medical Systems, ROCHE Group). Referring to FIG. 10c, mice treated with NK+ALT-803 (triangles, solid line) demonstrated a significant reduction in primary tumor volume compared to NK+IL2 treatment (squares, solid line) or to a vehicle control (PBS) (diamonds, dashed line). More specifically, at Day 21, mice treated with NK cells employing ALT-803 as cytokine support were found to have primary tumors from about 500 mm$^3$ to about 900 mm$^3$. In contrast, there was no statistical difference in tumor size for NK cell+IL-2 support and control only, both of which resulted in tumors over 2000 mm$^3$ in volume.

Figure 10D:
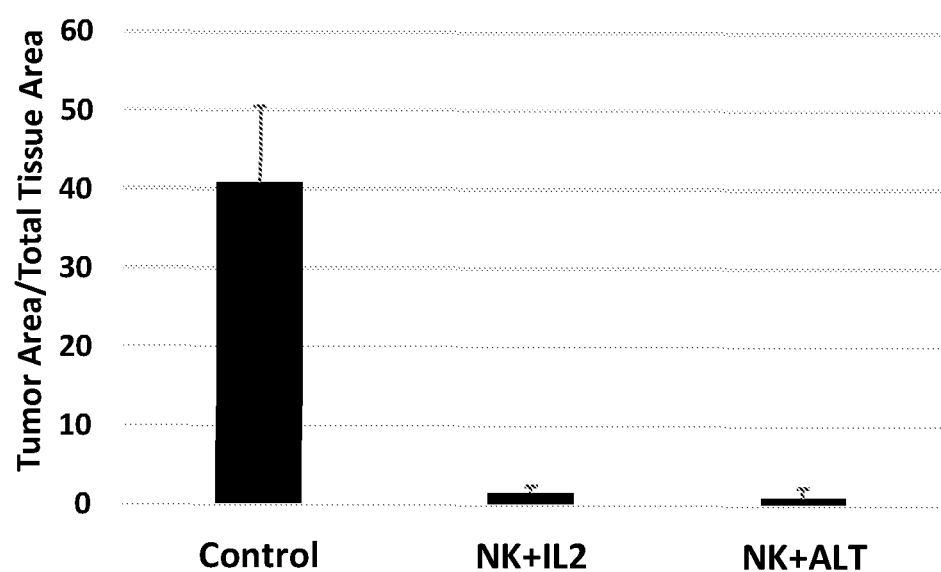
FIG. 10d provides quantification of lung tumors following treatment with control and NKF-expanded NK cells in the presence of IL-2 or ALT-803.
Figure 10E:
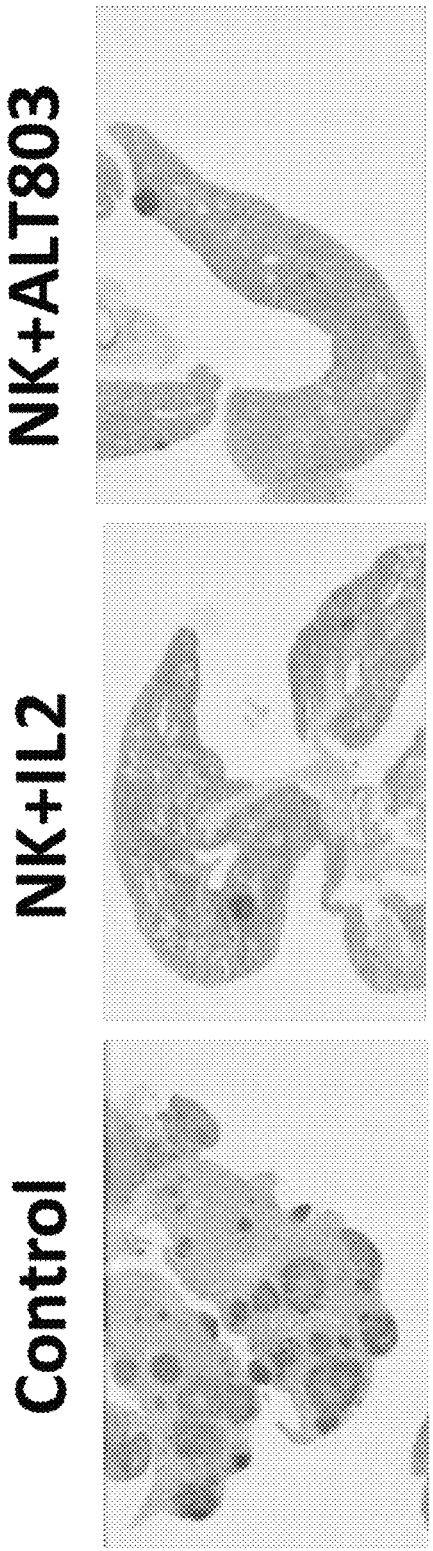
FIG. 10e shows Ki67 lung staining of lung metastases.
Figure 10F:
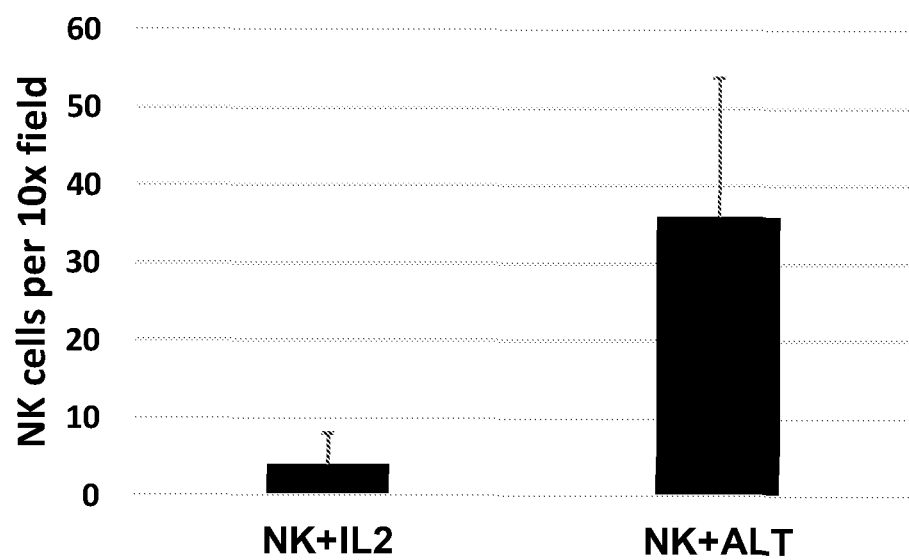
FIG. 10f compares the enhanced lung trafficking of NK cells provided with ALT-803 to NK cells provided with IL-2.

Referring to FIGS. 10d and 10e, NKF-expanded NK cell treatment (both ALT-803 and IL-2 treated groups) had dramatic reductions in lung metastases as seen by Ki67 stained tissue sections. FIG. 10d reports nearly a 40-fold reduction in lung metastases (based on the ratio of tumor area:total tissue area, y-axis) for NK cell-treatment regardless of cytokine support, as compared to control. FIG. 10e shows exemplary staining of control (left panel), NK+IL2 (center panel) and NK+ALT-803 (right panel) lung tumor metastases.

Human specific CD45 antibodies were used to monitor NK cell trafficking. Dissected lungs from the mice was fixed in formalin overnight and then paraffin blocks were prepared. The tissues were cut and slides were prepared from the paraffin blocks. Immunohistochemistry was performed by staining the slides with a human specific CD45 antibody to identify the human NK cells. Quantification of NK cell number (based on counting four 10× fields of lung tissue sections stained with CD45 antibodies) is presented in FIG. 10f and demonstrates that in mice treated with NK cells in combination with ATL-803 as cytokine support, significantly higher levels of NK cells were present in the lung (right bar) compared to NK-IL cells for mice treated with NK cells and IL-2 support (left bar). This suggests that ALT-803 demonstrates improved trafficking to the tumor site as compared to IL-2.

TGF-beta Inhibition Improves the Eefficacy of NK Cells in a Metastatic Colon Cancer Model.

While NK cells alone demonstrate efficacy in mouse models, it is known that tumor microenvironment factors impair NK cell function and limit their in vivo efficacy. One major immunoregulatory factor that regulates NK cell function is TGF-beta. Not only does TGF-beta markedly impair NK cell killing of cancer cells, but it can be readily reversed by TGF-beta inhibitors such as galunisertib.

Example 4—Effect of TGF-beta Inhibition on Cytotoxic Activity

Figure 11:
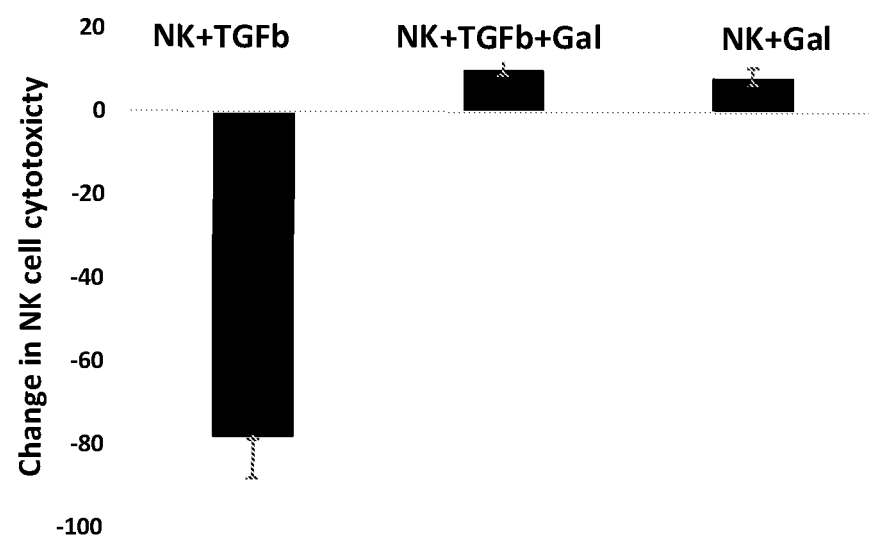
FIG. 11 is a graph showing the decreased in vitro cytotoxicity of NK cells in the presence of TGF-beta and the rescue of NK cell efficacy with co-administration of a TGF-beta inhibitor.

Referring to FIG. 11, expanded NK cells (K562 cells expressing mbIL-21) were treated with TGF-beta (5 ng/mL), galunisertib, or a combination thereof for 72 hours. The calcein-AM label flow cytometry assay described above was used against OCI-AML3 target cells at a 5:1 NK:target cell ratio to demonstrate that when NK cells are co-administered with TGF-beta, there is a drop in killing efficacy ranging from about 70% to about 90% (left bar). That drop can be rescued and reversed by co-administering NK cells with galunisertib (middle and right bars), in which case killing efficacy was improved by about 10%.

Figure 12A:
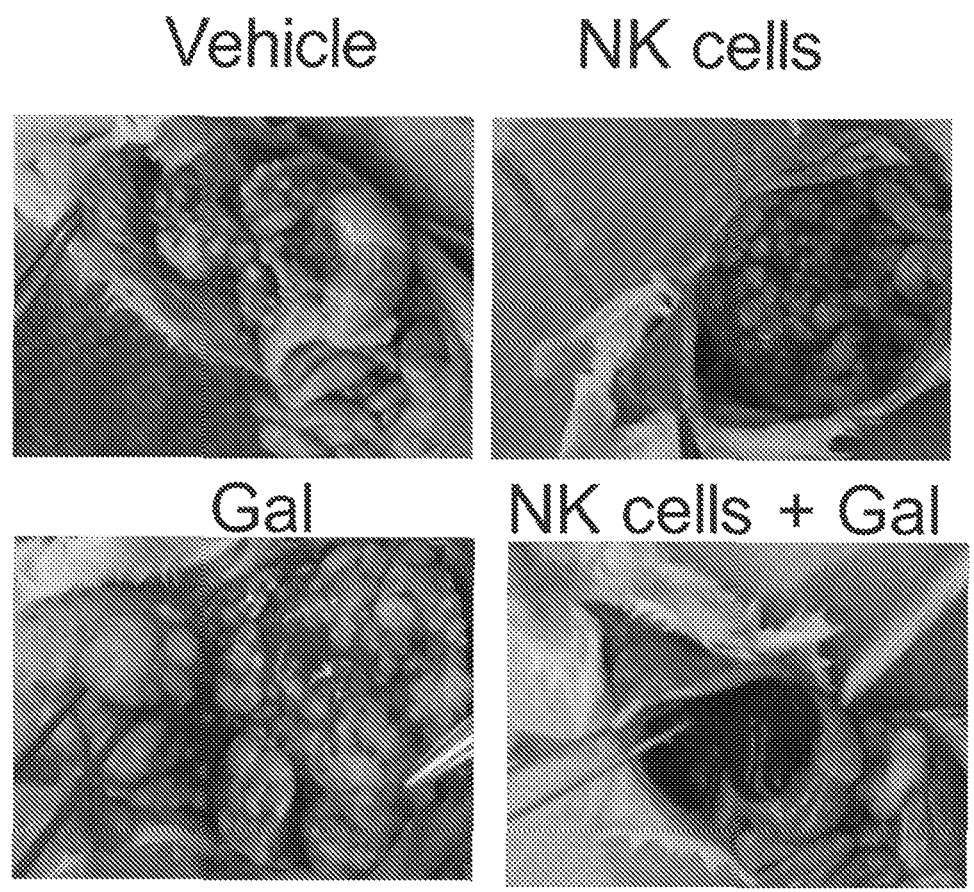
FIG. 12a shows exemplary tumor sections showing colon cancer metastases to the liver following treatment with vehicle, NK cells alone, a TGF-beta inhibitor alone or NK cells in combination with a TGF-beta inhibitor.
Figure 12B:
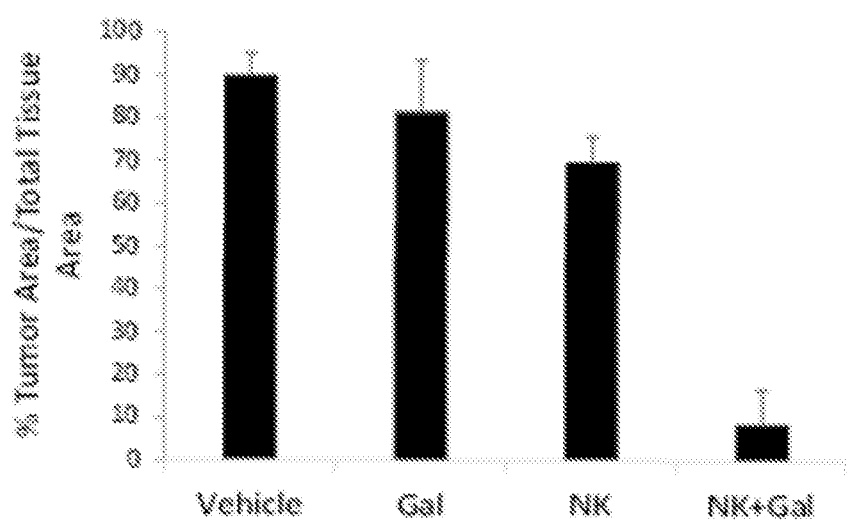
FIG. 12b shows the quantification of the liver sections of FIG. 12b, provided as the ratio of % tumor area:total tissue area.

Inhibition of TGF-beta also dramatically improves the in vivo activity of adoptively infused NK cells in a metastatic colon cancer model. NSG mice (n=5 per group) were injected into the spleen with HCT116 cells to initiate colon metastases to the liver followed by hemisplenectomy. The mice were treated with NK cells i.v., galunisertib (75 mg/kg daily PO) or both for 3 weeks. The mice were sacrificed after 4 weeks. Quantification of tumor in sections from the liver (n=4 per group) using Ventana Image Viewer. Referring to FIG. 12a, representative gross images are shown of liver tumor section following treatment with vehicle (top left panel), NK cells alone (top right panel), galunisertib alone (bottom left panel) and NK cells with concomitant administration of galunisertib (bottom right panel). These results are quantified in FIG. 12b as a ratio of % tumor area:total tissue are. Whereas the liver tumor burden of the control mice was about 90%, the concomitant administration of NK cells and galunisertib was about 10%.

What is claimed is:

1. A composition comprising acute myeloid leukemia (AML) cells engineered to express a membrane-bound interleukin (mbIL) protein, wherein the mbIL protein comprises the polypeptide sequence of SEQ ID NO:1.

2. The composition of claim 1, wherein the AML cells are OCI-AML3 cells.

3. The composition of claim 1, wherein the AML cells are HL-60 cells.

4. A composition comprising OCI-acute myeloid leukemia (AML) cells engineered to express a membrane-bound interleukin (mbIL) protein, wherein the mbIL protein has IL-21 activity and wherein the mbIL protein comprises the polypeptide sequence of SEQ ID NO:1.

5. The composition of claim 4, wherein the IL-21 activity is determined by improved expansion of NK cells as compared to NK cells in the absence of IL-21.

6. The composition of claim 5, wherein senescence of NK cells is reduced.

* * * * *